(12) United States Patent
Lee et al.

(10) Patent No.: US 6,174,918 B1
(45) Date of Patent: Jan. 16, 2001

(54) NAPHTHOQUINONE ANTITUMOR COMPOUND AND METHOD

(75) Inventors: Kuo-Hsiung Lee, Chapel Hill, NC (US); Sheng-Chu Kuo, Tai-Chung (TW); Toshiro Ibuka, Hirakata (JP)

(73) Assignee: The University of North Carolina at Chapel Hill, NC (US)

( * ) Notice: Under 35 U.S.C. 154(b), the term of this patent shall be extended for 0 days.

(21) Appl. No.: 09/126,624

(22) Filed: Jul. 30, 1998

Related U.S. Application Data

(62) Division of application No. 08/601,114, filed on Feb. 16, 1996, now Pat. No. 5,789,431.

(51) Int. Cl.[7] .......................... A61K 31/21; A61K 31/195; A61K 31/165; A61K 31/16; A61K 31/275; A61K 31/215

(52) U.S. Cl. .......................... 514/510; 574/563; 574/617; 574/625; 574/628; 574/629

(58) Field of Search .................................... 514/510, 563, 514/617, 625, 628, 629

(56) References Cited

PUBLICATIONS

Grundmann et al., Z. Krebsforsch.,72(2), pp 185–196 Abstract Only, 1969.*

\* cited by examiner

Primary Examiner—Jerome D. Goldberg
(74) Attorney, Agent, or Firm—Vincent M. Powers; LeeAnn Gorthey

(57) ABSTRACT

The invention provides 1,4-naphthoquinone compounds and a method for inhibiting tumor cell growth in a subject by administering such compounds. The compounds are represented by the structures:

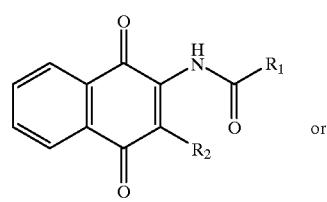

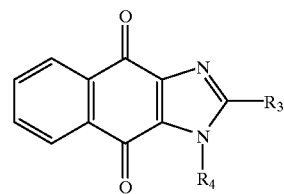

where $R_1$ is lower alkyl, halogenated lower alkyl, phenyl, benzyl, phenethyl, or —$(CH_2)_m$COOX, where m is 2 or 3 and X is H, methyl, or ethyl; $R_2$ is halo or NHY, where Y is hydrogen, loweralkyl, halogenated lower alkyl, hydroxylated lower alkyl, lower dialkylaminoalkyl, phenyl, benzyl, or phenethyl; $R_3$ is lower alkyl, halogenated lower alkyl, phenyl, benzyl, phenethyl, or —$(CH_2)_m$COOX, where m and X are as defined for $R_1$ above; and $R_4$ is hydrogen, lower alkyl, lower aminoalkyl, halogenated lower alkyl, phenyl, benzyl, or phenethyl.

15 Claims, 1 Drawing Sheet

NAPHTHOQUINONE ANTITUMOR COMPOUND AND METHOD

This application is a division of Ser. No. 08/601,114 filed Feb. 16, 1996, now U.S. Pat. No. 5,789,431 which is incorporated herein by reference.

This invention was made with Government support under grant CA 17625 awarded by the National Institutes of Health. Accordingly, the government has certain rights in this invention.

FIELD OF THE INVENTION

The present invention relates to 2,3-disubstituted naphthoquinone compounds and the use of such compounds as antitumor agents.

REFERENCES

Ambrogi, V., et al., *Br. J. Pharm.* 40:871 (1970).
Boyd, M., in *CANCER; PRINCIPLES AND PRACTICE OF ONCOLOGY UPDATES* (De Vita, V. T., et al., Eds.) J. B. Lippincott, Philadelphia, pp 1–12 (1989).
Driscoll, J., et al., *Cancer Chemother. Rep.* 4(2):1–27 (1974a).
Driscoll, J., *Canc. Chemo. Rep.* 4(4):3–4 (1974b).
Entwistle, I. D., et al., EP 240047 B1 (1987).
Fieser, L. F., et al., *Record Chem. Progress* 7:26 (1946).
Fries, K., et al., *Ann.* 516:248 (1935).
Gilman, A. G., et al., in *THE PHARMACOLOGICAL BASIS OF THERAPEUTICS*, Eighth Ed., Pergamon Press, New York, (1990).
Greene, T. W., et al., in *PROTECTIVE GROUPS IN ORGANIC SYNTHESIS*, 2nd Ed., John Wiley & Sons, New York, N.Y.(1991).
Grever, M. R. et al., *Seminars Oncol.* 19:622–638 (1992).
Griffin, J. E. and Wilson, J. D., (1991) in *HARRISON'S PRINCIPLES OF INTERNAL MEDICINE*, 12th Ed., (Harrison, T. R., et al., Eds.), McGraw-Hill, Inc., New York, N.Y., p 1587.
Hoffmann-Ostenhof, O., *Metab. Inhibitors* 2:145–159 (963).
Hoover, J. et al., *J. Am. Chem. Soc.* 76:4148–52 (1954).
Larock, R., in *COMPREHENSIVE ORGANIC TRANSFORMATIONS*, VCH Publishers, New York, N.Y., pp 972–976 (1989).
Lin, A., et al., *CANCER CHEMOTHER. REP.* 4(2):23–26 (1974).
Monks, A., et al., *J. Natl. Cancer Inst.* 83:757–766 (1991).
Morton, R. A., Ed., in *BIOCHEMISTRY OF QUINONES* Academic Press, New York, N.Y. (1965).
Webb, J. L., in *ENZYME AND METABOLIC INHIBITORS* Vol. 3, Academic Press, New York, N.Y. (1966).

BACKGROUND OF THE INVENTION

Compounds containing the quinone (cyclohexadienedione) moiety are involved in a wide variety of biochemical processes including electron transport and oxidative phosphorylation (Morton). Many quinone compounds are naturally occurring, such as o-benzoquinone, fumigatin (3-hydroxy-2-methoxy-5-methyl-1,4-benzoquinone), daunorubicin, adriamycin, lapachol, and phthiocol (2-hydroxy-3-methyl-1,4-naphthoquinone). The K vitamins are all 1,4-naphthoquinone compounds or compounds that are oxidized to contain the 1,4-naphthoquinone moiety and are present in the blood as coagulation factors. Another naturally occurring 1,4-naphthoquinone compound is coenzyme Q, which occurs in many kinds of cells and is involved in electron transport.

A wide variety of quinone derivatives have been synthesized to date, and various structurally diverse quinone compounds have been reported to be biologically active. As an illustration, various quinone compounds have been reported to possess enzyme inhibitory (Hoffmann-Ostenhof), antibacterial (Ambrogi), antimalarial (Fieser), metabolite antagonist (Hoover), and antifungal (Webb, Entwistle) activities.

Various synthetic and naturally occurring quinone compounds have been reported to exhibit antitumor properties. One example of such compounds, early recognized to exhibit antitumor properties, is the mitomycins, a group of antitumor antibiotics produced by *Streptomyces caespitosus* (griseovinaceseus). Included in this class is mitomycin C, an antineoplastic agent and inhibitor of nucleic acid synthesis (Lin). The mitomycins are heterocyclic quinone compounds, and the early discovery of the biological activity of these compounds has led to the synthesis and investigation of large numbers of heterocyclic quinone derivatives.

As part of its ongoing efforts to obtain new antitumor drug candidates, since the late 1950s, the National Cancer Institute (NCI) has screened over 700,000 synthetic compounds (Griffin). As part of this effort, the NCI has screened approximately 1500 quinones falling outside of the present invention, with limited success. Of the quinone compounds tested in in vivo and in vitro model systems, only a small number exhibited antitumor activity (Driscoll, 1974a,b). Further, in reviewing relationships among members of biologically active natural product families and model analogs thereof, such as in the case of quinones, it was concluded that structurally simpler analogs of complex active materials typically resulted in inactive compounds (Driscoll, 1974a), thus indicating the difficulty in designing compounds for use as antitumor agents.

In the United States, cancer is the second leading cause of death. Based on current statistics, an individual born in the United States has a greater than 1 in 3 chance of developing cancer in his or her lifetime. Since the mid-1950s, it has been recognized that cancer chemotherapy can be used to cure certain cancers. Although many cancers can be cured by surgical resection, chemotherapy is often used as an adjunct to surgical therapy, and is used primarily in the treatment of nonoperable or metastatic malignancy. In view of the high number of deaths each year resulting from cancer, a continuing need exists to identify effective chemotherapeutic drugs, and particularly compounds exhibiting high antitumor activity and selectivity, for use as anticancer agents.

SUMMARY OF THE INVENTION

The present invention provides a method for inhibiting tumor cell growth in a subject by administering a 1,4-naphthoquinone compound represented by the formula:

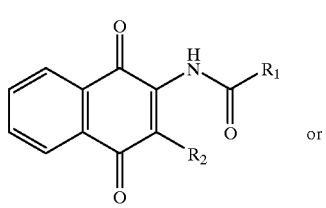

-continued

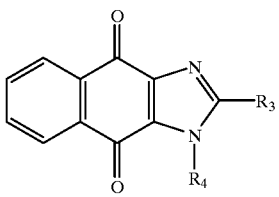

(II)

where $R_1$ is lower alkyl, halogenated lower alkyl, phenyl, benzyl, phenethyl, or —$(CH_2)_m COOX$, where m is 2 or 3 and X is H, methyl, or ethyl; $R_2$ is halo or NHY, where Y is hydrogen, lower alkyl, halogenated lower alkyl, hydroxylated lower alkyl, lower dialkylaminoalkyl, phenyl, benzyl, or phenethyl; $R_3$ is lower alkyl, halogenated lower alkyl, phenyl, benzyl, phenethyl, or —$(CH_2)_m COOX$, where m and X are as defined for $R_1$ above; and $R_4$ is hydrogen, lower alkyl, lower aminoalkyl, halogenated lower alkyl, phenyl, benzyl, or phenethyl.

In one embodiment, a 2-amido-3-substituted-1,4-naphthoquinone of formula (I) is administered where $R_1$ is phenyl or benzyl and $R_2$ is Cl. Compounds for administration according to the present invention are 2-amido-3-chloro derivatives having as $R_1$ a substituted phenyl group, where $R_1$ is 4-fluorophenyl, 4-methoxyphenyl, 3,5-dimethoxyphenyl, 2-fluorophenylmethyl, or 4-fluorophenylmethyl.

Additional compounds for administration by the present method are those represented by formula (I) where $R_1$ is phenyl and $R_2$ is NHY, where Y is hydrogen, methyl or ethyl, halogenated methyl or ethyl, hydroxyethyl, or —$(CH_2)_2 NZ_2$, where Z is methyl or ethyl. In a preferred embodiment, the compound is a 3-amino derivative where $R_1$ is 3,5-dimethoxyphenyl and $R_2$ is $NH(C_2H_5)$.

In yet another embodiment, compounds for use in inhibiting tumor cell growth are 2-amido-3-amino-1,4-naphthoquinones of formula (I), where $R_1$ is lower alkyl or halogenated lower alkyl, and $R_2$ is NHY, where Y is lower alkyl or halogenated lower alkyl. Representative compounds are those where $R_1$ is methyl and $R_2$ is NHCH $(CH_2CH_3)_2$ or $NHCH_2CH_2N(CH_3)_2$.

Additional 2-amido-3-substituted-1,4-naphthoquinones of formula (I) for use in the present treatment method are those where $R_1$ is lower alkyl, halogenated lower alkyl, or —$(CH_2)_m COOX$, and $R_2$ is NHY, where Y is phenyl or benzyl. In one embodiment, $R_1$ is methyl, and Y is (4-methoxyphenyl)methyl or (4-chlorophenol)methyl. In another embodiment, $R_1$ is —$(CH_2)_2 COOCH_3$ or —$(CH_2)_2 COOCH_2CH_3$, and $R_2$ is NHY, where Y is unsubstituted phenyl or 4-methoxyphenyl.

In another embodiment of the present invention, a 1,2-disubstituted naphth[2,3-d]imidazole-4,9-dione of formula (II) is administered, for inhibiting tumor cell growth in a subject. 1,2-disubstituted naphth[2,3-d]imidazole-4,9-dione compounds for administration according to the present method are those where $R_3$ is phenyl or benzyl, and $R_4$ is H. Additional compounds for use in the present invention are those where $R_3$ and $R_4$ are both lower alkyl groups. In a preferred embodiment, $R_3$ is methyl and $R_4$ is ethyl. In another embodiment, $R_3$ is methyl and $R_4$ is 2-chloroethyl.

Additional compounds represented by formula (II), for use in the present method are those where $R_3$ is lower alkyl, halogenated lower alkyol, or —$(CH_2)_m COOX$, and $R_4$ is phenyl or benzyl. In one embodiment of the invention, growth of tumor cells is inhibited by administering a compound represented by formula (II) where $R_3$ is methyl and $R_4$ is 4-methylbenzyl. In an alternate embodiment, $R_3$ is phenyl or benzyl, and $R_4$ is lower alkyl.

The method of the present invention further includes administering to a subject, a 2-amido-3-substituted-1,4-naphthoquinone or 1,2-disubstituted naphth[2,3-d]imidazole-4,9-dione compound of the type described above, in an amount effective to inhibit tumor growth in the treated subject.

In another aspect, the present invention includes a compound represented by formula (I) or (II), for use in inhibiting tumor cell growth in a mammalian subject.

The compounds show high cytotoxic activity against a variety of tumor cell lines, such as leukemia, non-small cell and small cell lung, colon, central nervous system (CNS), melanoma, ovarian, prostate, breast and renal cancer cell lines.

The invention further includes a pharmaceutical composition which contains either a 2-amido-3-substituted-1,4-naphthoquinone or 1,2-disubstituted naphth[2,3-d]imidazole-4,9-dione compound of the type described above, for use in inhibiting the growth of tumor cells.

These and other objects and features of the invention will become more fully apparent when the following detailed description of the invention is read in conjunction with the accompanying drawings.

BRIEF DESCRIPTION OF THE FIGURES

The FIGURE illustrates two different synthetic routes for synthesizing the compounds of the present invention.

DETAILED DESCRIPTION OF THE INVENTION

I. Definitions

Figure 1:
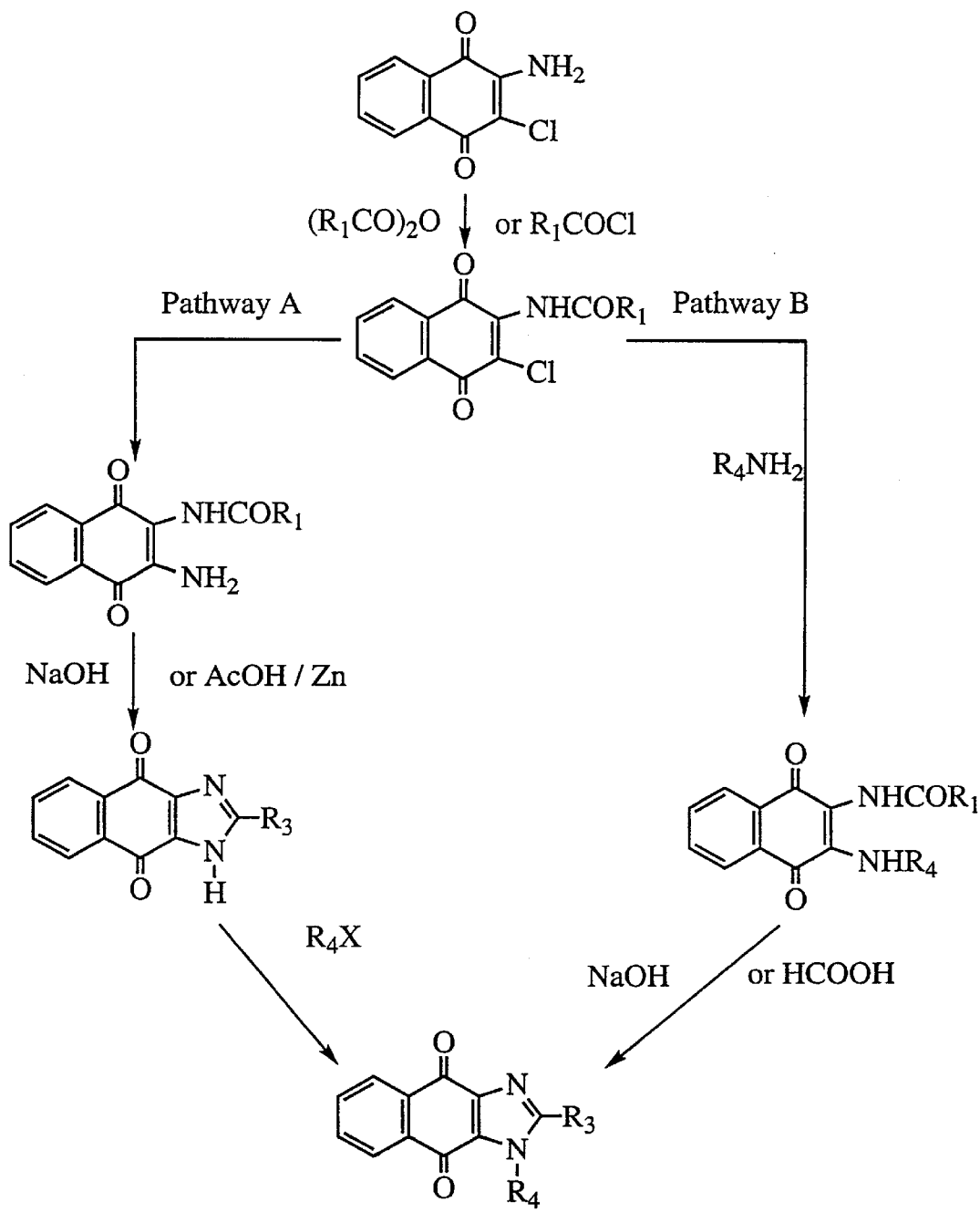

The following terms, as used herein, have the meanings as indicated:

"Alkyl" refers to hydrocarbon chains, typically ranging from 1 to 12 carbon atoms in length. The hydrocarbon chains may be saturated or unsaturated and may optionally contain additional functional groups attached thereto, such as hydroxyl or halo. The hydrocarbon chains may be branched or straight chain. Exemplary alkyl groups include ethyl, propyl, 1-methylbutyl, 1-ethylpropyl and 3-methylpentyl.

"Lower alkyl" refers to an alkyl groups containing from 1 to 5 carbon atoms, and may be straight chain or branched, as exemplified by methyl, ethyl, n-butyl, i-butyl, t-butyl, including fluorinated, monohydroxy, or chlorinated forms thereof.

"Lower aminoalkyl" refers to a lower alkyl group containing one or more amino substituents, where the amino substituent may be mono-, di-, or trisubstituted to contain one or more additional lower alkyl groups as described above.

As used herein, "halogen", "halo group" or "halide" refers to a group VIIA atom selected from F, Cl, Br and I, and is preferably F or Cl.

By "phenyl" is meant substituted or unsubstituted phenyl, wherein the phenyl group may be substituted with one or more substituents selected from halo, alkyl (as defined above), lower alkyl (as defined above) such as $CH_3$, $CH_2Cl$, $CHCl_2$, $CCl_3$, $CH_2F$, $CHF_2$, $CF_3$); nitro, hydroxy, alkoxy, such as $OCF_3$, or $OCH_3$; amino, primary amino, secondary amino, tertiary amino, quaternary ammonium, carboxy or carboxylate, acetoxy, cyano, and sulfhydryl. The substituents may be in any orientation on the phenyl ring (i.e., ortho, meta or para). For substituents carrying a formal charge, it is understood that the resulting compound will contain a pharmaceutically acceptable counterion, such as bromide, iodide, acetate, methanesulfonate, succinate, hydrogen sulfate, or citrate.

"Benzyl" refers to a substituted or unsubstituted phenylmethyl group, where phenyl is as defined above, and the methyl group may be optionally substituted with one or more halogens or $C_1$ or $C_2$ lower alkyl groups.

"Quinone" refers to any compound containing a cyclohexadiendione structural unit, and particularly a p-benzoquinone unit.

As used herein, "dialkylaminoalkyl" refers to a substituent having the general structure —(R')NR"R"', where R' indicates the point of attachment, and R', R", and R"' are all alkyl as defined above.

"Phenethyl" refers to 2-phenylethyl, where phenyl is as defined above.

The structures below indicate the numbering system employed herein to refer the 2-amido-3-substituted-1,4-naphthoquinone (I) or 1,2-disubstituted naphth[2,3-d]imidazole-4,9-dione (II) compounds of the invention.

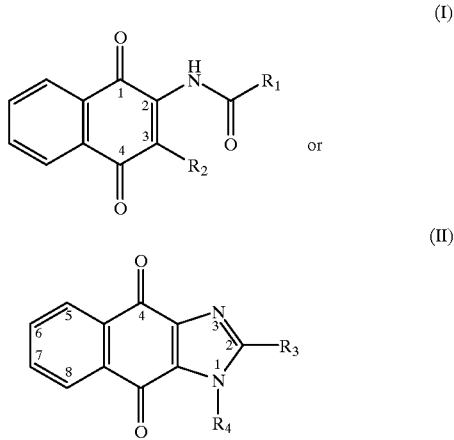

Structure (II) includes protonated forms in which the 3-nitrogen atom is protonated to form the corresponding imidazolium salt. In cases in which structure (I) or structure (II) contains one or more amino groups in either substituent $R_1$ or $R_2$, or $R_3$ or $R_4$, respectively, the structure is meant to include protonated forms thereof. In instances in which a substituent in structure (I) or structure (II) compounds of the invention contains one or more carboxy groups, by carboxy is meant the acid and salts thereof.

II. 2,3-Disubstituted Naphthoquinones

This section describes the 2,3-disubstituted naphthoquinone compounds of the present invention and synthetic methods for preparing these compounds. The 2,3-disubstituted naphthoquinone compounds are useful in the treatment of tumors, particularly solid tumors.

The naphthoquinone compounds of the invention are generally described by structures (I) and (II) above. Compounds represented by structure (I) are referred to herein as 2-amido-3-substituted-1,4-naphthoquinones, while compounds represented by structure (II) are generally referred to as 1,2-disubstituted-naphth[2,3-d]imidazole-4,9-diones.

With reference to these structures, the compounds of the present invention all include a central naphthoquinone moiety, having substituents at the 2 and 3 positions. Compounds described by structure (I) possess an amido group at the 2-position, while the substituent at the 3-position is typically halo or amino. The 2-amido group is generally of the form —NHC(O)—$R_1$, where $R_1$ is lower alkyl, halogenated lower alkyl, phenyl, benzyl, phenethyl, or —(CH$_2$)$_m$COOX, where m is 2 or 3 and X is H, methyl, or ethyl. The substituent at the 3-position, represented by $R_2$, includes compounds where $R_2$ is halo or NHY, and Y is hydrogen, lower alkyl, halogenated lower alkyl, hydroxylated lower alkyl, lower dialkylaminoalkyl, phenyl, benzyl, or phenethyl. The compounds described by structure (I) may be used as intermediates in preparing the 1,2-disubstituted-naphth[2,3-d]imidazole-4,9-diones of the present invention.

The imidazole derivatives of 1,4-naphthoquinone illustrated generally by structure (II) possess a tricyclic ring structure, with an imidazole ring fused to the central naphthoquinone moiety. The naphth[2,3-d]imidazole-4,9-diones of the invention include compounds with substituents at the 1- and optionally at the 2 position. Substituents at the 1-position are represented herein by the symbol $R_4$ while substituents at the 2 position are indicated by the symbol $R_3$. Exemplary compounds illustrated by structure (II) include those where $R_3$ is lower alkyl, halogenated lower alkyl, phenyl, benzyl, phenethyl, or —(CH$_2$)$_m$COOX, where m and X are as defined for $R_1$ above. Typically, $R_4$ is hydrogen, lower alkyl, lower aminoalkyl, halogenated lower alkyl, phenyl, benzyl, or phenethyl.

A. Preparation of Structure I Compounds: 2-Amido-3-Substituted-1,4-Naphthoquinones The preparation of compounds having the general structure represented by (I) is described below.

The 2-amido-3-chloro-1,4-naphthoquinones of the invention are typically prepared from 2-amino-3-chloro-1,4-naphthoquinone (Aldrich, Milwaukee, Wis.), as described in Examples 1A.1–5. The starting material, 2-amino-3-chloro-1,4-naphthoquinone, can be transformed into any of a number of 2-amido-derivatives by reaction with a carboxylic acid (Larock) or an activated carboxylic acid derivative, such as an acid anhydride or acid chloride (Hoover), possessing the desired $R_1$ group, with yields ranging from about 55–98% (Table 1). For example, exemplary anhydrides for use in preparing the structure (I) compounds of the invention have the formula, (R$_1$CO)$_2$O, where $R_1$ is lower alkyl, halogenated lower alkyl, phenyl, benzyl, phenethyl, or —(CH$_2$)$_m$COOX, where m is 2 or 3 and X is H, methyl, or ethyl. In instances in which the desired $R_1$ group contains a carboxy functionality (i.e., X=H), the anhydride reagent typically contains the carboxy group in protected form, which is then deprotected subsequent to transforming the 2-amino functionality to the corresponding 2-amido group.

The above synthetic approach for preparing the structure (I) compounds of the invention is illustrated in the top portion of the figure. As shown in Examples 1A.1–2, exemplary 2-acetamido- (2a), 2-propanamido- (2c) and 2-butanamido-3-chloro-1,4-naphthoquinone (2d) compounds are prepared by acylaton of the 2-amino starting material with the corresponding acid anhydride in the presence of concentrated sulfuric acid. Acid anhydride reagents that may be used to prepare compounds 2a, 2c and 2 d are acetic anhydride, propionic anhydride and butanoic anhydride, respectively. Any of a number 2-amido derivatives may be similarly prepared.

Following a similar approach, exemplary compounds 2b, 2k, and 2l are prepared by reacting 2-amino-3-chloro-1,4-naphthoquinone with the appropriate acyl chloride in the presence of an acid catalyst to form the desired structure (I)

compounds, as shown in Example 1A.3. Typically, the acid catalyst employed is either concentrated sulfuric acid or dry HCl, although dry hydrogen chloride is reported to be the more effective catalyst (Hoover). The acid chloride reagent may optionally possess additional functional groups, as illustrated by the representative methyl ester acid chlorides, ClC(O) $(CH_2)_m COOH_3$, where m is 2 or 3, respectively. Such functionalized acid chlorides are used to prepare compounds such as 2k and 2l, as illustrated in Example 1A.3.

In selecting an acid chloride reagent for preparing the compounds of the invention, any functional group present in addition to the acid chloride moiety of the reagent should be stable under the reaction conditions employed, or alternately, may be present in a protected form which is stable under acidic conditions. Any of a number of protecting groups may be utilized to protect acid-labile functionalities, as described in Greene. A suitable protecting group for this use, and for general use in preparing any of the compounds of the invention, is one which is easy to introduce into the molecule, protects the reactive group under the reaction conditions employed, and is removable under conditions (either acidic or basic) which leave the resulting 2-,3-disubstituted naphthoquinone compound intact.

Compounds such as the exemplary 2-amidoaryl functionalized 1,4-naphthoquinone compounds 2e and 2i are prepared by acylation of the reactive 2-amino group of the 2-amino-3-chloro-1,4-naphthoquinone starting material. In this synthetic approach, an acyl chloride such as benzoyl chloride or 2-fluorophenylacetyl chloride is used to convert the 2-amino functionality into the corresponding amide, as illustrated in Examples 1A.4–5.

In some instances, it may be preferable to carry out the acylation reaction under basic conditions, since some compounds, such as the 2-benzoylamino-3-chloro-1,4-naphthoquinone compounds 2e–2h, are resistant to acylaton under strongly acidic conditions, even with prolonged heating times. In carrying out a base-promoted N-acylation reaction, the starting material is typically treated with a strong base such as NaH, followed by addition of the acid chloride reagent to promote acylation at the reactive amino nitrogen. This synthetic approach is shown in Example 1A.4 for the preparation of 2e–2h, and typically results in good yields. For example, under basic conditions, N-acylation of 1 occurs readily to give an 80% yield of 2-benzoylamino-3-chloro-1,4-naphthoquinone (2e).

In another approach, a Lewis acid catalyst such as boron trifluoride etherate is used to promote N-acylation, as shown in Example 1A.5 for the preparation of exemplary compound 21.

The above 2-amido-3-chloro-1,4-naphthoquinones have been shown to possess unexpectedly high selectivity and cytotoxicity against a variety of tumor cell lines, as will be described in section IIIA below. These compounds may also be used as intermediates in the preparation of the 2-amido-3-amino-1,4-naphthoquinone and 1,2-substituted naphth[2,3-d]imidazole-4,9-dione compounds of the present invention.

Synthesis of the 3-amino functionalized 1,4-naphthoquinones represented by structure (I) is typically carried out by amination of the corresponding 2-amido-3-chloro-1,4-naphthoquinone with either ammonia or a primary amine (Hoover), to replace the 3-chloro atom with an amino group, as illustrated in Examples 1B.1–2, and in the figure.

The 3-amino compounds 3a, 3b and 3c are synthesized by reacting the corresponding 3-chloro precursors, 2a, 2i and 2j, respectively, with dry ammonia gas, in nitrobenzene. For introduction of an amino group into the 1,4-naphthoquinone ring system, nitrobenzene is the preferred solvent of use (Hoover), although many other solvents such as dioxane or toluene may also be used.

Introduction of a secondary amino group at the 3-position of the 1,4-naphthoquinone ring system is similarly carried out by reacting a 2-acylamino-3-chloro-1,4-naphthoquinone precursor with an excess of a primary amine. In preparing the 2-acylamino-3-amino-1,4-naphthoquinone compounds of the invention, an amine having the formula $H_2NY$ is typically used, where Y is lower alkyl, halogenated lower alkyl, hydroxylated lower alkyl, lower dialkylaminoalkyl, phenyl, benzyl, or phenethyl. Exemplary primary amines useful in preparing the compounds of the present invention include lower alkyl amines such as methylamine, ethylamine, sec-butylamine, isobutylamine, t-butylamine, sec-pentylamine, and (1-ethyl)propylamine, and halogenated or hydroxylated forms thereof, such as ethanolamine and (2-chloro)ethylamine. Additional amine reagents include phenyl or benzyl amines such as para-methoxybenzylamine and para-chlorobenzylamine. Exemplary primary amines useful in preparing the compounds of the invention are illustrated in Table 2, column 2, under the heading "$R_2$", where for the purpose of determining the amine used to aminate the starting material, $R_2$ is considered to represent "$NH_2Y$", with each of the column entries corresponding to the "Y" portion of the amine.

The 3-amino compounds may optionally be prepared as the corresponding acid salts, typically as the HCl salts, although any pharmaceutically acceptable counterion may be used (such as bromide, iodide, acetate, methanesulfonate, succinate, hydrogen sulfate, or citrate). In some instances, protonation of the amino nitrogen may be desirable for increasing the solubility of the compounds in the delivery vehicle. Alternatively, the 3-amino substituent may be alkylated, such as with a lower alkyl halide, to form the corresponding quaternary ammonium compound.

Preparation of compounds 29, 30–43, and 44–56 is described in Example 1B.2.

B. Preparation of Structure II Compounds: Preparation of 1,2-Substituted Naphth[2,3-D]Imidazole-4,9-Diones Imidazole compounds of the present invention having the general structure represented by (II) are typically prepared by cyclization of a 2-amido-3-amino-1,4-naphthoquinone (such as those described in section A above) in which the amino substituent in the 3-ring position is either —$NH_2$, or is an alkylamino or arylamino group, such as lower alkylamino, halogenated alkylamino, phenylamino, benzylamino, or phenethylamino. Alternately, the dione may be generated by oxidation of naphth(2,3)imidazole, such as with chromic acid (Fries).

The naphth[2,3-d]imidazole-4,9-diones of the invention can be synthesized by two different routes, designated as Pathway A or Pathway B, as illustrated in the figure.

Both routes involve cyclization of a 2-amido-3-amino-1,4-naphthoquinone precursor to form the imidazole portion of the resulting naphth[2,3-d]imidazole-4,9-dione ring system, although in Pathway A (figure), the precursor possesses a 3-amino (—$NH_2$) group, which is optionally alkylated (or arylated) subsequent to cyclization by reaction with an alkyl or aryl halide, to introduce the desired $R_4$ functionality into the final product. In instances in which the starting compound is resistant to alkylation, a trialkyl or triaryl oxonium salt such as trimethyl or triethyl oxonium tetrafluoroborate may be used as the alkylating agent.

In an alternative approach, as shown by Pathway B in the figure, the cyclizaton reaction is carried out on a 2-amido-3-amino-1,4-naphthoquinone compound possessing a secondary alkylamino or arylamino group in the 3-position of the naphthoquinone ring, which upon cyclization, provides the 1-substituent ($R_4$) in the imidazole ring of the desired naphth[2,3-d]imidazole-4,9-dione product.

Conversion of 2-acylamino-3-amino-1,4-naphthoquinones to the corresponding imidazoles can be carried out under either basic (e.g., NaOH) or acidic (e.g., Zn/acetic acid) conditions, as in Examples 2A.1–2.

Briefly, in the base-promoted cyclizaton procedure, a 2-acylamino-3-amino-1,4-naphthoquinone is heated in alcohol containing an aqueous solution of a base, such as sodium hydroxide, to form the corresponding imidazole. As an illustration, exemplary compounds 4a, 4b, and 4c are prepared by cyclization of the corresponding 2-acylamino-3-amino-1,4-naphthoquinones 3a, 3b, and 3c, respectively, under basic conditions, as shown in Example 2A.1. The representative naphth[2,3d]imidazole-4,9-dione compounds 4b and 4c, containing fluorinated benzyl groups at the C-2 position and hydrogen at the N-1 position, are typically prepared using Route A.

As can be seen, any of a number of 2-substituted imidazole compounds can be synthesized by this method by varying the $R_1$ substituent of the 2-acylamino-3-amino-1,4-naphthoquinone starting material. Preferred starting materials are those in which $R_1$ is lower alkyl, halogenated lower alkyl, phenyl, benzyl, phenethyl, or —$(CH_2)_m$COOX, where m is 2 or 3 and X is methyl, or ethyl.

The imidazole compounds prepared as in Example 2A.1 (4a, 4b, and 4c) are all unsubstituted at the 1-position, although the above base-catalyzed procedure may also be used to form the 1-substituted compounds of the invention directly, in which the $R_4$ substituent is as described above. As has been described, alkylation can be carried out at the imino position (1-position) of the imidazole ring to form any of a number of 1-alkyl or 1-aryl derivatives. As illustrated in Example 2A.2, compound 4a, 2-methyl-1H[2,3-d] imidazole-4,9-dione, is alkylated by addition of iodoethane under basic conditions to form the corresponding 1-ethyl derivative, 5.

The reaction of compounds 4b and 4c with an equimolar ratio of both NaH and ethyl iodide results in ethylation at N-1 forming exemplary compounds 63 and 66, respectively. The use of two molar equivalents of NaH and excess ehtyl iodide results in compounds 64 and 65, which contain a second ethyl group at the benzyl carbon.

A variety of substituents can be introduced into the 1-position of the resulting imidazole, as illustrated in Example 2A.2. As illustrated in Example 2A.2, exemplary compounds 17, 19, and 20, each containing a different $R_4$ group, are similarly prepared by reacting compound 4a with a variety of alkyl iodides (e.g., I—$CH_2$—p—$(C_6H_5)CH_3$, I—$CH_2$—p—$(C_6H_5)$F, and I—$CH_2$—p—$(C_6H_5)$Cl). Exemplary substitutents which may be present at the N-1 position in the compounds of the present invention (i.e., substituent $R_4$) include lower alkyl, lower aminoalkyl, halogenated lower alkyl, phenyl, benzyl, or phenethyl, as illustrated by the compounds listed in Tables 3 and 4. Table 4 contains a sub-grouping of compounds also included in Table 3. The compounds shown in Table 4 all possess an ethyl group substituted at the N-1 position of the imidazole ring.

Many of the compounds of the present invention are synthesized by Route B, which can be used to provide both the precursor (i.e., the 2-acylamino-3-amino-1-4-naphthoquinones) and the resulting imidazole compounds, both classes of which were discovered to contain compounds possessing unexpectedly high cytotoxic activity. Further, Route B typically provides better yields of the 1,2-substituted naphth [2,3-d]-imidazole-4,9-diones of the invention and easier workup procedures than does Route A.

As shown in Example 2A.2, compound 5 can be prepared by the Route B method. In synthesizing the product by this route, compound 2a is first reacted with ethylamine to form 2-acetamido-3-ethylamino-1,4-naphthoquinone (29), which is cyclized with NaOH affording 5.

As shown in the figure, the imidazole ring formation reaction can be effected under either acidic or basic conditions. Compounds 21–29 are prepared by cyclization in formic acid from the correspond 2-acylamino-3-amino-1,4-maphthoquinone intermediates, as shown in Example 2A.3.

Compounds 57–62, which contain a terminal carboxylic acid functionality in the C-2 position, are prepared from the corresponding methyl ester precursors, 51–56, using Route B.

The 1,4-naphthoquinone compounds of the present invention can be prepared using the synthetic methodologies described in section II above, as further illustrated in Examples 1 and 2. Tables 1–4 include yields and relevant characterization data (melting point, mass spectroscopy data, $M^+$ ion, UV, IR and $^1$H NMR chemical shift values, including assignments) for several exemplary 1,4-naphthoquinone compounds of the present invention.

III. TREATMENT METHOD

The present invention includes a method of inhibiting tumor cell growth in a subject by administering to a subject a 1,4-naphthoquinone compound of the type described in section II above. In one embodiment of the present invention, a 2-amido-3-substituted-1,4-naphthoquinone illustrated by formula (I) is administered for inhibiting tumor cell growth. In an alternate embodiment, a 1,2-disubstituted naphth[2,3-d]imidazole-4,9-dione of formula (II) is administered, for inhibiting tumor cell growth in a subject.

Compounds of the invention are found to exhibit unexpectedly high levels of activity and selectivity when screened in vitro for cytotoxicity against a number of cancer cell lines, as will be described below.

A. Screening-Evaluation of Compounds for Tumor Cell Toxicity

To evaluate the compounds of the invention for use in inhibiting tumor cell growth, several of the compounds were screened in vitro for cytotoxic activity against a number of cancer cell lines including ovarian (Table 5), non-small cell lung (Table 6), central nervous system (Table 7), melanoma (Table 8), colon (Table 9), leukemia (Table 10), prostate (Table 11), small cell lung (Table 12), breast (Table 13), and renal (Table 14) cancers. The 67 specific cell lines used in the cytotoxicity assay are listed in Example 3 and in Tables 5–13. This assay involves determination of a test agent's effect of growth parameters against a panel of approximately 60 cell lines derived from human cancers, which consist largely of solid tumors and a few leukemia lines. The cytotoxicity results are expressed as log $GI_{50}$ (growth inhibition) values, representing the log molar drug concentration required to cause 50% inhibition. Preferred compounds for use in the invention are those exhibiting log$GI_{50}$ values less than about −4.

Some of the cell lines, including OVCAR-3 ovarian cancer, NCI-H522 non-small cell lung cancer, several melanomas, HCT-116 colon cancer, and HL-60 leukemia, exhibit significant sensitivity to the compounds of the present invention over that of normal cells, indicating the overall potential efficacy of the present compounds in treating tumors containing cells of these types.

In an examination of the results of the cytotoxicity screening, several of the compounds display potent cytotoxicity against a number of different types of cancer cell lines. The 1-ethyl-2-methyl imidazole compound, 1-ethyl-2-methylnaphth-[2,3-d]imidazole-4,9-dione, (5) shows good activity and high selectivity in four ovarian cancer cell lines ($logGI_{50}$ values ranging from −6.1 to −7.3 in OVCAR-3, -4, -5, and -8 cell lines, Table 5). Selectivity is also found in the small cell lung cancer cell line DMS-114 ($logGI_{50}$=−6.56, Table 12). In each of the general classifications of cancer types screened in vitro (i.e., ovarian, non-small lung, CNS, etc.), compound 5 displays potent cytotoxicity in one or more of the representative cell lines tested. Looking at Table 6, compound 5 illustrates good cytotoxicity against each of the cell lines tested, and is highly active against non-small cell lung NCI-H522 cells ($logGI_{50}$=−6.62). Similarly, compound 5 is highly active in inhibiting growth of CNS SF-268 cells ($logGI_{50}$=−6.48, Table 7). Compound 5 shows similarly high cytotoxicity against colon cancer cells (COLO-205, $logGI_{50}$=−6.45; SW 620, $logGI_{50}$=−6.17; Table 9) and breast cancer cells (MCF-7, $logGI_{50}$=−6.17). Additionally, compound 5 has been selected by NCI for testing in an in vivo tumor xenograft model. The above results indicate that compound 5 is a preferred compound for use in inhibiting tumor cell growth, and preferably growth of tumor cells of the type described above.

In considering exemplary 1,2-disubstituted naphth[2,3-d] imidazole-4,9-dione derivatives containing various alkyl, benzyl, or phenyl groups at the C-2 or N-1 positions (i.e., $R_3$ or $R_4$ substituents), when the C-2 substituent is fixed as a methyl group ($R_3$=methyl, as in compounds 6–14) and larger and increasingly branched alkyl groups are inserted at the N-1 position, in comparison to compound 5 (which exhibited $logGI_{50}$ values in the range of −6 to −7 in most cell lines), compounds 6–14 show somewhat decreased activities, with $logGI_{50}$ values generally in the range of −4 to −5 in ovarian, non-small lung, CNS, colon, and small cell lung cancer cells. The observed activities for 6–14 are similar for melanoma and leukemia cancer cells. In summary, 2-methyl-naphth[2,3-d]imidazole-4,9-dione derivatives containing branched alkyl or aryl groups at N-1 inhibit tumor cell growth in ovarian, non-small lung, CNS, colon, and small cell lung cancer cells, although these compounds are not as effective as compound 5 in inhibiting growth of cancer cells.

In continuing an examination of the cytotoxicities displayed by various exemplary 1,2-disubstituted naphth[2,3-d]imidazole-4,9-dione derivatives containing a methyl group at the 2-position (i.e., $R_3$=$CH_3$, see Table 3, compounds 4a, 5–21), compounds 15, 16, and 21 each contain a beta substituted ethyl group at N1, where the substituent is a polar group such as dimethylamino, hydroxy, or chloro, respectively (i.e., $R_4$=$CH_2CH_2$-polar group). The activities of these compounds are comparable to those of compounds 6–14.

Representatives 2-methyl-naphth[2,3-d]imidazole-4,9-diones containing a para-substituted benzyl group at N1, i.e., 17, $R_4$=p-methylbenzyl; 18, $R_4$=p-chlorobenzyl); 19, $R_4$=p-fluorobenzyl; 20, $R_4$=p-chlorobenzyl), show slightly higher activities ($logGI_{50}$ values of −5 to −6) than the corresponding N1-ethyl-substituted compounds in non-small cell lung, CNS, melanoma, colon, leukemia, small cell lung, and renal cancer cell lines. Compound 17 is a potent growth inhibitor of tumor cells of the following types: non-small cell lung, where for NCI-H460 cells, $logGI_{50}$=−6.41 (Table 6); melanoma, where for LOX1MVI cells, $logGI_{50}$=−6.22; (Table 8); colon cancer, where for HCT-116 cells, $logGI_{50}$=−6.12 and for HCT-15 cells, $logGI_{50}$=−6.21, (Table 9); and leukemia, where for K-562 cells, $logGI_{50}$=−6.08, and for MOLT-4 cells, $logGI_{50}$=−6.19, and in SR cells, $logGI_{50}$=−6.48 (Table 10).

The above results indicate that 2-methyl-naphth[2,3-d] imidazole-4,9-diones containing a para-substituted benzyl group at N1 are preferred for use in inhibiting tumor cell growth. One such preferred compound for use in inhibiting growth of cancer cells is compound 17. This class of compounds, as exemplified by compound 17, is especially useful in inhibiting growth of non-small cell lung, melanoma, colon and leukemia cancer cells of the type described above.

Now considering naphth[2,3-d]imidazole-4,9-diones which do not contain a methyl group at C-2, naphth[2,3-d] imidazole-4,9-diones possessing a fixed ethyl substituent at N-1 (i.e., $R_4$=$C_2H_5$) and various C-2 substituents were also evaluated for cytotoxicity against tumor cells. Compounds with ethyl (23), propyl (24), phenyl (25), p-fluorophenyl (26), p-methoxyphenyl (27), and 3,5-dimethoxyphenyl (28) $R_3$ groups are, in general, effective in inhibiting cancer cell growth, although these compounds are somewhat less active ($logGI_{50}$ values around −5) than the C-2 methyl imidazole compounds discussed above. Imidazole compounds containing an N-1 ethyl group (i.e., $R_4$=$C_2H_5$) and having as $R_3$, a halogenated benzyl group, which may be alkylated at the benzyl carbon, such as exemplary compounds 63–66, display activity profiles comparable to those of compounds 23–28.

Compound 22, containing a substituted methyl group at C-2, ($R_3$=$CH_2Cl$) and an N-1 ethyl group, is highly cytotoxic against cancer cells, with $GI_{50}$ values ranging from −6 to −6.8. Structure (II) compounds, where $R_4$ is ethyl and $R_3$ is lower alkyl containing one or more polar substituents, as exemplified by compound 22, are preferred for use in the present method. As illustrated by the results in Tables 5, 6, 8, and 10, compound 22 is a potent cytotoxic agent, and is active against each of the cancer cell types tested. Specifically, compound 22 is highly effective in inhibiting growth of the following cancer cell types, including ovarian cancer, non-small cell lung cancer, CNS cancer, melanoma, and leukemia.

In general, representative compounds 57–62, in which the $R_3$ substituent contains a terminal polar group such as carboxy, and $R_4$ is any of a number of substituents, such as benzyl, substituted benzyl, or phenyl, are cytotoxic against tumor cells, displaying cytotoxicities similar to those of the corresponding non-carboxy containing $C_2$-derivatized naphth[2,3-d]imidazole-4,9-dione compounds.

Considering now the biological activity of exemplary structure (I) compounds of the invention, several 2-acylamino-3-alkylamino-1,4-naphthoquinone compounds, e.g., 29–50, were evaluated for cytotoxic activity. Compounds 29–43 are all 2-acetamido compounds (i.e., $R_1$=methyl) containing various 3-alkylamino groups in the $R_2$ or 3-ring position. In general, these compounds are cytotoxic against cancer cells, with log $GI_{50}$ values in the cancer cell panel assay ranging from approximately −4 to −5. One of the representative compounds, 34, is highly cytotoxic against non-small cell lung cancer cells, HOP-92 cells, as shown in Table 6 (log $GI_{50}$=−6.47), and is a preferred compound for inhibiting growth of non-small cell lung cancer cells.

Naphthoquinone compounds 44–50 each contain an ethylamino (—NHCH$_2$CH$_3$) group at R$_2$, with various alkyl, halogenated alkyl, phenyl, and substituted phenyl groups as the R$_1$ substituent. These compounds are also cytotoxic against tumor cells, exhibiting activities in the representative cancer cell line panel, as indicated by log GI$_{50}$ values typically ranging from −4 to −5. IN further considering this series of compounds, 50, containing a dimethoxybenzoyl group as R$_1$, demonstrates significant activity in all cancer cell lines (logGI$_{50}$ values less than −6) except for small cell lung cancer cells. Based on this result, 2-acylamino-3-alkylamino-1,4-naphthoquinones having an alkylamino group as R$_2$, preferably an ethylamino group, and a disubstituted phenyl group as R$_1$, preferably substituted with polar substituents such as methoxy or ethoxy, are one group of preferred compounds for use in inhibiting tumor cell growth by the present method.

Compound 50, a representative 2-acylamino-3-alkylamino-1,4-naphthoquinone compound having an alkylamino group as R$_2$ and a distributed phenyl group as R$_1$, is effective in inhibiting growth of a variety of tumor cells types, as illustrated in Tables 5–11 and 13. Compound 50 demonstrates potent cytotoxic activity against ovarian cancer cells, non-small cell lung cancer, CNS cancer, melanoma, renal cancer, colon cancer, leukemia, prostate cancer, and breast cancer.

Also evaluated for biological activity were a group of structure (I) compounds where R$_1$ is a lower alkyl methyl ester group, and R$_2$ is phenylamino (including substituted phenylamino) or a benzylamino group, as exemplified by compounds 51–56. These compound display cytotoxicities in the cancer screening assay, as indicated by log GI$_{50}$ values typically ranging from about −5 to −5, as shown in Tables 5–11 and 13.

Cytotoxic evaluation of the 2-acylamino-3-chloro-1,4-naphthoquinones of the invention (Table 1) verified the antitumor properties of these compounds. While the 2-benzoylamino compound, 2e, shows good activity in the cancer cell line panel (logGI$_{50}$ values ranging from −4 to −5), addition of a p-fluoro (2f) or a p-methoxy (2g) group significantly increases the activity (logGI$_{50}$ values generally aroung −6) in most cell lines. The 3,5dimethoxy substituted compound, 2h, shows similarly potent cytotoxic activity. Compounds 2i and 2j contain phenylacetamido groups fluorinated at the ortho and para positions, respectively. Both of these compounds display high activity in many cell lines with logGI$_{50}$ values ranging from −5.6 to −7.6.

Replacement of the 3-chloro group of 2i and 2j with an NH$_2$ group results in compounds 3b and 3c, which display significantly reduced cytotoxicity against tumor cells (3b and 3c are inactive against all representative cancer cell lines) in comparison to the parent chloro compounds.

In summary, both the structure (I) and structure (II) compounds of the invention are effective in inhibiting tumor cell growth, as exemplified by the representative in vitro screening results described above. With reference to the structure (I) compounds in Tables 1 and 2, R-group features which promote high cytotoxic activity against cancer cells (log GI$_{50}$ values less than −6) are: a halo or lower alkylamino group for R$_2$; and substituted phenyl or benzyl at the R$_1$ position, where one or more of the phenyl substituents is a polar group such as a halide or alkoxy group. The exemplary acylamino-3-alkylamino-1,4-naphthoquinone, 50, shows high activity and selectivity and is a preferred compound for use in inhibiting tumor cell growth. Similarly, significant antitumor activity is displayed by several representative 2-acylamino-3-chloro-1,4-naphthoquinone precursor compounds, 2f–2j, also preferred for use in inhibiting tumor cell growth.

Similarly for the structure (II) compounds, as shown in Tables 3 and 4, features which promote high cytotoxicity against cancer cells include: a lower alkyl or substituted lower alkyl group at R$_3$, in combination with a lower alkyl or benzyl (including ring-substituted benzyl) at the R$_4$ position. One preferred lower alkyl group at the R$_3$ position is methyl or substituted methyl, where the methyl group contains an electronegative group such as a halide or a lower alkoxy or hydroxy group, as can be seen from the potent cytotoxicities against tumor cells displayed by compounds 5, 17 and 22. Preferred for use in the present method are compounds which, in addition to possessing an R$_3$ group as described above, possess an ethyl group at R$_4$, such as compounds 5 and 22. Another preferred substituent at R$_4$ is benzyl, where the aromatic ring contains an electrodonating group such as methyl. Within this group of structure (II) compounds, 5, with an ethyl group at N-1 (R4) and a methyl group at C-2 (R3) is the most active naphth[2,3-d]imidazole-4,9-dione derivative of the exemplary structure (II) type compounds tested, while the imidazole compounds 17 and 22 are also highly active against many of the cancer cell types tested.

These preferred R-groups are intended to provide guidance in the selection of R groups at the R$_1$–R$_4$ positions, for optimizing compound efficiency.

B. Treatment Methods

In accordance with the invention, 2,3-disubstituted naphthoquinone compounds invention are administered to inhibit tumor cell growth in a mammalian subject. The composition of the invention typically includes the 2,3-disubstituted naphthoquinone compound contained in a pharmaceutical carrier which is suitable for oral, topical or parenteral administration of the antitumor compound. The composition may contain one or a combination of 2,3-disubstituted naphthoquinone compounds, and may further include a compound for modulating drug resistance. Agents known to modulate drug resistance include calcium channel antagonists, polyene antibiotics, and antiarrhythmic drugs, for example.

The method of the present invention is for the treatment of both solid tumors and blood-born tumors. A solid tumor is defined as one that grows in an anatomical site outside the bloodstream (in contrast, for example, to blood-born tumors such as leukemias) and requires the formation of small blood vessels and capillaries to supply nutrients, etc. to the growing tumor mass.

In the method of the invention, a 2-amido-3-substituted-1,4-naphthoquinone of formula (I) or a 1,2-disubstituted naphth[2,3-d]imidazole-4,9-dione of formula (II) is administered in a pharmaceutically effective amount, to inhibit tumor growth in a mammalian subject. By pharmaceutically effective amount is meant a concentration of active agent at the tumor site or in the bloodstream which is effective to inhibit growth of tumor cells. This concentration can be determined from EC$_{50}$ values from in vitro growth inhibition studies, using known tumor cell lines, and is related to the patient's tumor type. Thus, for many applications, an effective dose is preferably one which produces a concentration of antitumor compound in this range at the tumor site.

The main routes of drug delivery, in the treatment method are intravenous, oral, and topical, as will be described below.

Other drug-administration methods, such as subcutaneous injection or via inhalation, which are effective to deliver the drug to a target site or to introduce the drug into the bloodstream, are also contemplated.

1. Pharmaceutical Compositions Containing 2,3-Disubstituted Naphthoquinones

Formulations containing the naphthoquinone compounds of the invention may take the form of solid, semi-solid, lyophilized powder, or liquid dosage forms, such as, for example, tablets, pills, capsules, powders, solutions, suspensions, emulsions, suppositories, retention enemas, creams, ointments, lotions, aerosols or the like, preferably in unit dosage forms suitable for simple administration of precise dosages.

The compositions typically include a conventional pharmaceutical carrier or excipient and may additionally include other medicinal agents, carriers, adjuvants, and the like. The antitumor compounds can be prepared in a pharmaceutically acceptable salt form according to standard methods, e.g., by acid/base titration or exchange with suitable counterions such as $K^+$, $Na^+$, $Mg^+$, or the like, for anionic antitumor compounds, or with sulfate, chloride, or other suitable anions for potentially cationic antitumor compounds.

Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. The composition may take the form of a solution, suspension, tablet, pill, capsule, powder, sustained-release formulation, and the like.

The active compound of formula (I) or (II) may be formulated into a suppository comprising, for example, about 0.5% to about 50% of a compound of the invention, disposed in a polyethylene glycol (PEG) carrier (e.g., PEG 1000 [96%] and PEG 4000 [4%].

Liquid compositions can be prepared by dissolving or dispersing the naphthoquinone compound (about 0.5% to about 20%), and optional pharmaceutical adjuvants in a carrier, such as, for example, aqueous saline, aqueous dextrose, glycerol, ethanol and the like, to form a solution or suspension. The antitumor compounds may be formulated into a retention enema.

If desired, the composition to be administered may also contain minor amounts of non-toxic auxiliary substances such as wetting or emulsifying agents, pH buffering agents, such as, for example, sodium acetate, sorbitan monolaurate, or triethanolamine oleate.

Methods for preparing such dosage forms are known or will be apparent to those skilled in the art; for example, see *Remington's Pharmaceutical Sciences* (1980). The composition to be administered will contain a quantity of the pro-drug and/or active compound(s) in a pharmaceutically effective amount for inhibiting growth of tumor cells when administered in accordance with the teachings of this invention.

The discussed above, the main routes of drug delivery in the treatment method are intravenous, oral, and topical, as will be described below.

2. Parenteral Administration

An injectable composition for parenteral administration will typically contain the naphthoquinone compound in a suitable IV solution, such as sterile physiological salt solution. A dosage of a 2-amido-3-substituted-1,4-naphthoquinone (I) or 1,2-disubstituted naphth[2,3-d]imidazole-4,9-dione (II) compound is selected to produce the target mid-range concentration at the tumor site, according to known pharmacokinetic models (Gilman). Dosages effective to achieve this range of concentrations in the blood in human patients can be readily determined from animal model studies, using known dose relationships between dose and pharmacokinetics between animal models and humans.

For example, compound doses in the range of 0.05 to 5.0 µg/ml are generally effective to reduce tumor growth for a large number of tumor-cell types. So, for a naphthoquinone compound of the type described above, given a representative target tumor concentration from about 0.05 to 5.0 µg/ml, reflecting a target midpoint of 0.50 µg/ml, an approximate $EC_{50}$ value of 0.50 µg/ml is determined. Accordingly, a parenteral dose of naphthoquinone compound is chosen to achieve such a cytotoxic concentration in the bloodstream, or more preferably, in the tumor.

In conjunction with such pharmacokinetic calculations, an appropriate solid animal tumor model can be selected, animals dosed with varying doses of compounds, and the resulting intra-tumor concentrations determined, according to standard analytical methods. From this information, a correlation can be made between blood levels of compound and intra-tumor concentration. Likewise, using the same experimental model, a plasma clearance rate can be determined for the naphthoquinone compound of interest.

3. Intra-tumor injection of 2-amido-3-substituted-1,4-naphthoquinone of formula (I) or a 1,2-disubstituted naphth[2,3-d]imidazole-4,9-dione of formula (II)

For use in the treatment of solid tumors, and in instances in which the tumor region is accessible to hypodermic delivery of antitumor agent, it may be desirable to inject the naphthoquinone compounds directly into the tumor. This administration method has the advantage of largely eliminating the need for pharmacokinetic estimations, as required for parenteral injection, and decreases the amount of drug required as well as reduces the systemic effects of the agent.

The amount and volume of naphthoquinone compound to be administered will mostly depend on the size of the tumor, but may also be affected by tissue metabolism of active compound at the site of injection Generally, the desired volume used in this mode of administration will be proportional to the volume of the tumor target region, and will not exceed more than about half the volume of the tumor. Moreover, the volume as well as the dose of compound administered will be calculated to take into consideration metabolism and excretion of drug, according to standard pharmacological principles. Accordingly, the naphthoquinone compound should be present in a concentration sufficient to provide an effective cytotoxic concentration in the tumor, as described in Subsection 2, above.

4. Administration of Naphthoquinones by Catheter

The 2,3-disubstituted naphthoquinone compounds of the invention can also be delivered to a tumor site by catheter. Generally, standard catheters suitable for delivery of active agent may be used; however, in some cases, it may be desirable to use specialized catheters, such as double-balloon catheters.

In the catheter delivery methods described, it may also be desirable to include as part of the injectable composition, a radio-opaque contrast agent which allows the material to be monitored fluoroscopically after embolization. Representative contrast agents include various iodine-containing organic compounds such as diatrizoate meglumine, diatrizoate sodium, ipodamide meglumine, iothalamate meglumine, iothalamate sodium, metrizoic acid, methiodal sodium. Tantalum powder and barium sulfate also be used for this purpose. Many of these agents are supplied commercially in sterilized solution or in suspension form, at a concentration of between about 20–80 weight percent contrast agent, for use in X-ray fluoroscopy.

5. Topical Administration

The 2,3-disubstituted naphthoquinone compounds of the invention can also be delivered topically. For topical administration, a composition containing between 1–5% or more 2,3-disubstituted naphthoquinone compound is generally suitable. Regions for topical administration include the skin surface and also mucous membrane tissues of the vagina, rectum, nose, mouth, and throat. Compositions for topical administration via the skin and mucous membranes should not give rise to signs of irritation, such as swelling or redness.

The topical composition may include a pharmaceutically acceptable carrier adapted for topical administration. Thus, the composition may take the form of a suspension, solution, ointment, lotion, sexual lubricant, cream, foam, aerosol, spray, suppository, implant, inhalant, tablet, capsule, dry powder, syrup, balm or lozenge, for example. Methods for preparing such compositions are well known in the pharmaceutical industry.

6. Dosage Regime

During tumor treatment, the patient will typically receive periodic doses, e.g., biweekly doses of the drug, with the effectiveness of treatment being monitored by tumor biopsy, radiological methods, or blood enzyme levels, according to standard methods. The dosage requirements will vary with the particular drug composition employed, the route of administration, tumor type, the cytotoxic agent employed, and the particular subject being treated. Ideally, a patient to be treated by the present method will receive a pharmaceutically effective amount of antitumor compound in the maximum tolerated dose, generally no higher than that required before drug resistance develops. Preferably, the chemotherapeutic agent is delivered in frequent doses to reduce the emergence of drug-resistant cancer cells.

From the foregoing, it can be appreciated how the treatment method of the invention offers advantages in tumor treatment. The compounds of the invention are readily synthesized, can be administered by a number of routes, e.g., either orally or parenterally. The naphthoquinone compounds of the invention are cytotoxic to cancer cells, and have high antitumor activity for a broad range of cancer cell types, making them suitable for broad antitumor use.

The following examples illustrate, but in no way are intended to limit the scope of the present invention.

EXAMPLES

Materials and Methods

Infrared (IR) samples were prepared as KBr pellets. IR spectra were obtained using a Shimadzu IR-440 spectrometer. $^1$H NMR spectra were obtained on JEOL FX-90Q or Varian VXR-300 FT NMR spectrometers. NMR samples were dissolved in $CDCl_3$ or $DMSO-d_6$ (as indicated) using tetramethylsilane (TMS) as an internal standard. Chemical shift values are reported in δ (ppm) relative to tetrametylsilane $(CH_3)_4Si$. The following abbreviations were used to characterized the observed splitting patterns and appearance of peaks: s=singlet, d=doublet, t=triplet, q=quartet, m=multiplet, and br=broad. Mass spectra (MS) were obtained using a Hewlett Packard 5995 GC-MS instrument. Samples for UV characterization were dissolved in ethanol and UV spectra were recorded on a Shimadzu UV-160A UV-visible recording spectrophotometer. Reported melting point values are uncorrected. s Elemental analyses were performed by National Cheng Kung University and National Chung Hsing University, Taiwan.

Example 1

Synthesis of 2,3-Disubstituted Naphthoquinones

A. STRUCTURE (I) COMPOUNDS: 2-ACYLAMINO-3-CHLORO-1,4-NAPHTHOQUINONES 1. 2-Acetamido-3-chloro-1,4-naphthoquinone (2a). To a suspension of 2-amino-3-chloro-1,4naphthoquinone (1) (52 g, 0.25 mol) in acetic anhydride (75 ml) were added 5 drops of concentrated $H_2SO_4$. The reaction mixture was stirred at room temperature for 20 min and then filtered. The precipitate was washed with $Et_2O$ and recrystallized from EtOH, forming golden needle crystals (mp 219°–220° C.) of 2a in a 98% yield. Spectral data is summarized in Table 1 (See Appendix).

2. 2-Propanamido-3-chloro-1,4-naphthoquinone (2c) and 2-Butanamido-3-chloro-1,4-naphthoquinone (2d). Compounds 2c and 2d were similarly prepared using 1 as the starting material along with the appropriate acid anhydride. Physical and spectral data are given in Table 1.

3. 2-Chloroacetamido-3-chloro-1,3-naphthoquinone (2b). To a suspension of 2-amino-3-chlorol,4-naphthoquinone (1) (10.4 g, 0.05 mol) in anhydrous xylene (100 mL) was added 50 ml of chloroacetyl chloride and dry HCl. The reaction mixture was refluxed for 40 minutes, and allowed to cool to room temperature over a period of 6 h. An equivalent volume of $Et_2O$ was added to the reaction flask, and the flask was stored for one day until a precipitate formed. The precipitate was recovered by filtration, and recrystallized from benzene to yield 2b as light yellow needle crystals (85% yield). Physical and spectral characterization data are presented in Table 1.

Compounds 2k and 2l were similarly prepared by reacting 1 with the appropriate acid chloride. Yields and compound characterization data are provided in Table 1.

4. 2-Benzoylamino-3-chloro-1,4-naphthoquinone (2e). To a solution of 2-amino-3-chloro-1,4naphthoquinone (1) (1.0 g, 4.8 mmol) in tetrahydrofuran (50 ml) was added 0.2 g sodium hydride at room temperature. The reaction mixture was stirred for 30 min, followed by addition of 1 g of benzoyl chloride. The resulting mixture was stirred for an additional 5 minutes. The reaction mixture was then poured into ice water and extracted with $CHCl_3$. The chloroform extracts were combined and the solvent was removed by rotary evaporation to yield a crude oil. The residue was column chromatographed on silica gel using benzene as the eluent. The purified produce, 2e, was recovered in 80% yield. Characterization data are given in Table 1.

Compounds 2f–2h were similarly prepared. Yields, melting points, and spectral data are provided in Table 1.

5. 2-(2-Fluorophenyl)acetamido-3-chloro-1,4-naphthoquinone (2i). To a stirred mixture of 2-amino-3-chlorol,4-naphthoquinone (1) (16.6 g, 0.080 mol) and 2-fluorophenylacetyl chloride (17.2 g, 0.1 mol) was added 3 mL of $BF_3$●$Et_2O$, and the resulting mixture was refluxed for 24 h. The mixture was then concentrated under reduced pressure to yield a crude semi-solid, to which was added 50 ml of acetone. Stirring was continued for 20 min under reflux. After cooling, the precipitate was collected by filtration and washed with acetone. Recrystallization from DMF:acetone (1:1) gave 18 g (66% yield) of 2i as yellow crystals. Melting point and spectral data are given in Table I.

Compound 2j was similarly prepared. Yield, melting point, and spectral data are given in Table 1.

B. STRUCTURE (I) COMPOUNDS: 2-ACYLAMINO-3-ALKYLAMINO-1,4-NAPHTHOQUINONES AND 2-ACYLAMINO-3-ARYLAMINO-1,4-NAPHTHOQUINONES 1. 2-Acetamido-3-amino-1,4-naphthoquinone (3a). Compound 2a (8.5 g, 0.34 mol) was dissolved in anhydrous nitrobenzene (300 mL), to which dry $NH_3$ gas was added, and the reaction mixture was then heated at reflux for 1 h. After cooling, the resulting precipitate was filtered and recrystallized from EtOH to give dark red needles of 3a (mp 233°–234° C., 92% yield). Spectral data are provided in Table 2.

Compounds 3b and 3c were prepared in an analogous manner from 2i and 2j, respectively. Yields, melting points, and spectral data are summarized in Table 2.

2. 2-Acetamido-3-ethylamino-1,4-naphthoquinone (29). To a suspension of 2a (5.0 g, 0.02 mol) in toluene (100 mL) was added an excess of ethylamine. The reaction mixture was stirred for 30 min at room temperature. The precipitate was recovered by filtration, followed by recrystallization from ethanol to form dark red crystals of 29 (88% yield). Physical and spectral data are given in Table 2.

Compounds 30–43 were similarly prepared from 2a.

Compounds 44–56 were similarly prepared from 2b–2h, 2k or 2l as starting material, depending upon the substituent at the 2 position in the parent naphthoquinone compound. Yields, melting points, and spectral data are summarized in Table 2.

Example 2

Synthesis of 1,2-Substituted Naphth [2,3-D] imidazole-4,9-Diones

A. STRUCTURE (II) COMPOUNDS 1. 2-Methyl-1H-naphth[2,3-d]imidazole-4,9-dione (4a). Method 1 (Base-Promoted Cyclization): To a solution of 3a (4.0 g, 0.017 mol) in EtOH (50 ml) was added 2N NaOH (20 ml) and the resulting mixture was refluxed for 24 h. The reaction mixture was then cooled and filtered. The recovered precipitate was recrystallized from EtOH to give 4a as a dark brown powder (mp 360°–370° C.) in a 98% yield. Spectral data are given in Table 3.

Compounds 4b and 4c were synthesized in the same manner utilizing 3b and 3c, respectively, as starting materials. Yields, mps, and spectral data are given in Table 3.

Method 2 (Acid-Promoted Cyclization): A solution of 3a (2.0 g, 0.0009 mol) and Zn (1.0 g) in glacial acetic acid (50 ml) was refluxed for 24 h. A small amount of activated charcoal was added, and the solution was then filtered. The filtrate was poured into a 4-fold excess of $H_2O$. The pH was adjusted to 8 by addition of a solution of $NaHCO_3$, and the resulting solution was then filtered. The recovered precipitate was recrystallized from EtOH to give a dark brown powder (4a).

2. 1-Ethyl-2-methylnaphth[2,3-d] imidazole-4,9-dione, (5). Route A: A solution of 4a (2.0 g, 9.4 mmol) in a small amount of DMF was heated to 40°–50° C. to which was added 1.0 g of NaOH, and the heating continued until the NaOH dissolved. After cooling to room temperature, an equimolar amount of iodoethane was added, and stirring continued for 1 h. The reaction mixture was then poured into ice water, filtered, and purified by column chromatography ($CHCl_3$ eluent, silica gel solid support). Recrystallization of the product (5) from EtOH gave yellow crystals. Yield, mp, and spectral data are presented in Table 3.

Compounds 17, 19 and 20 were also prepared from 4a using an analogous procedure; yields, mps, and spectral data are given in Table 3.

Route B: To a solution of 29 (4.0 g, 0.017 mol) in EtOH (50 ml) was added a solution of 2N NaOH. The reaction mixture was refluxed for 30 min, then cooled and filtered. The recovered precipitate was washed with $H_2O$, dried, and recrystallized from EtOH:$CHCl_3$ to afford the same product (5) as obtained by Method 1.

Compounds 6–16, 18, and 20 were prepared similarly in two steps 2a and the appropriate alkylamine via intermediates 30–42. Compounds 57–62 were also prepared in an analogous fashion from 51–56. Yields, mps, and spectral data are given in Table 3.

3. 1-(2'-Chloroethyl)-2-methylnaphth [2,3-d] imidazole-4,9-dione (21). A solution of 43 (5 g, 0.02 mol, prepared from 2a and 2-chloroethylamine in an analogous manner to that of 29 below) in formic acid (50 ml) was refluxed for 1 h, and then concentrated. Purification by column chromatography ($CHCl_3$, silica gel), followed by recrystallization from benzene, afforded 21 as yellow crystals. Yield, mp, and spectral data are given in Table 3.

Compounds 22–28 were synthesized by the same method from 2b–2h and ethylamine via intermediates 44–50. Yields, mps, and spectral data are given in Table 3.

4. 1-Ethyl-2-(2'-fluorophenyl) methylnaphth[2,3-d] imidazole-4,9-dione (63). To a stirred suspension of 28.8 mg (1.2 mmol) of NaH in 1 mL of anhydrous DMF maintained at 0° C., was added a solution of 306 mg (1 mmol) of 4b in 3 ml of DMF. The mixture was stirred for 15 min, followed by addition of ethyl iodide (0.3 ml). The resulting mixture was stirred for 3 h at room temperature. Ice-water (2 mL) was added, and the mixture was extracted with $CHCl_3$. The organic extract was washed with water, dried over anhydrous $MgSO_4$, and concentrated under reduced pressure. The crude product, a brown oil, was purified by flash chromatography on silica gel with n-hexane-EtOAc (4:1) to yield 240 mg (72%) of the title compound. Recrystallization from a $CHCl_3$-$Me_2CO$ (1:5) afforded yellow crystals, mp 176° C. Spectral data are given in Table 3.

Following a procedure identical to that described for the synthesis of 63, 4c was converted to 66. Compounds 64 and 65 were prepared in a similar manner from 4b and 4c, respectively, using 2 molar equivalents of NaH and an excess of ethyl iodide. Yields, mps, and spectral data are reported in Table 3.

Example 3

Tumor-Cell Cytotoxicity Activity

A. INITIAL IN VITRO CYTOTOXICITY SCREENING AGAINST KB CELL GROWTH

Compound 5 was assayed for in vitro cytotoxicity against KB cells in culture, following the protocol of Monks. The KB cell line was obtained from the American Type Culture Collection, Rockville, Md., and cells were adapted to grow in antibiotic-free RPMI-1640 medium supplemented with 10 fetal calf serum.

The ED$_{50}$ value was calculated mathematically from 2 data points across 50% inhibition in cell growth. Compound 5 showed good activity with an ED$_{50}$ value of <0.40 μg/ml.

B. IN VITRO CYTOTOXICITY SCREENING AGAINST A PANEL OF HUMAN CELL LINES

Based upon the results from the initial screening of 5 described above, 5 was submitted for evaluation in the NCI's in vitro disease-oriented anti-tumor screen, which determines a test agent's effect on growth against a panel of approximately 60 human tumor cell lines (Grever, Monks, Boyd), including leukemia, non-small cell and small cell lung, colon, CNS, melanoma, ovarian, and renal cancers. Cytotoxicity results are expressed as log GI$_{50}$ values, representing the log molar drug concentration required to cause 50% inhibition. Cytotoxicity data for 5 are shown in Tables 5–7, 9, 12, and 13.

Based upon the good activity and high selectivity exhibited by 5 in the cytotoxicity assays (see in particular, Tables 5–7, 9, 12, and 13), additional compounds of the present invention were similarly evaluated for cytotoxicity in NCI's anti-tumor screen.

Cell lines used to screen cytotoxicity again ovarian cancer cell growth included IGROV-1, OVCAR-3, OVCAR-4, OVCAR-5, OVCAR-8, and SK-OV-3. The results are shown in Table 5.

Cell lines used to examine inhibition of non-small cell lung cancer cell growth included EKVX, HOP-18, HOP-62, HOP-92, NCI-H266, NCI-H23, NCI-H460, NCI-H522, and LXFL-529. The results are shown in Table 6.

Inhibition of in vitro CNS cancer cell growth was examined using the following cell lines: SF-268, SF-295, SF-539, SNB-19, SNB-75, SNB-78, U 251 and XF-498. The results are given in Table 7.

For screening inhibition of melanoma cell growth by the present compounds, the following cell lines were utilized: LOX1MVI, MALME3M, M14, M19-MEL, SK-MEL-2, SK-MEL-28, SK-MEL-5, UACC-257, and UACC-62. The results are indicated in Table 8.

Human cell lines used to investigate the effects of the present compounds on colon cancer cell growth in vitro include COLO-205, DLD-1, HCC-2998, HCT-116, HCT-15, HT 29, KM 12, KM 20L2, SW620. The results are summarized in Table 9.

Cell lines used to test in vitro inhibition of leukemia cell growth by the present compounds were CCRF-CEM, HL-60 (TB), K-562, MOLT-4, RPMI-8226, and SR. The results are shown in Table 10.

Table 11 illustrates in vitro inhibition of prostate cancer cell growth using cell lines PC-3 and DU-145.

Cell lines used to screen inhibition of small cancer cell growth were DMS 114 and DMS 273; results are summarized in Table 12.

Cell lines used to investigate in vitro inhibition of breast cancer cell growth were the following: MCF-7, MCF7-ADR-RES, MDA-MB-231/ATCC, HS 578T, MDA-MB-435, MDA-N, BT-549, T-47D. The cytotoxic effects of the present compounds upon breast cancer cell lines are shown in Table 13.

Human cell lines used to investigate the effects of the present compounds on renal cancer cell growth in vitro were the following: 786-0, ACHN, CAKI-1, RXF-393, RXF-631, SN12C, TK-10, and UO-31, as illustrated in Table 14.

Although the invention has been described with respect to particular embodiments, it will be appreciated that various changes and modifications can be made without departing from the invention.

TABLE 1

2-Acylamino-3-chloro-1,4-naphthoquinones

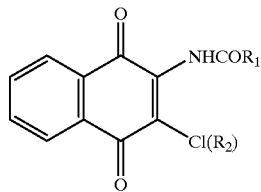

| No. | R$_1$ | Yield (%) | mp °C. | MS (M$^+$) m/z | UV λ max (log ε) | IR υ$_{C=O}$ | $^1$H-NMR (ppm) |
|---|---|---|---|---|---|---|---|
| 2a | —CH$_3$ | 98 | 219–220 | 249.5 | 253 (4.26) | 1670 1700 | 2.31(3H, s, —COCH$_3$), 7.71(1H, br, —NH), 7.73–7.82(2H, m, H-6,7), 8.10–8.13(2H, m, H-5), 8.18–8.20(2H, m, H-8) |
| 2b | —CH$_2$Cl | 85 | 167–169 | 284 | 270 (4.32) | 1665 1700 | 4.24(2H, s, —COCH$_2$Cl), 7.24–7.78(2H, m, H-6,7), 8.09–8.12(1H, m, H-5), 8.13–8.18(1H, m, H-8) |
| 2c | —CH$_2$CH$_3$ | 92 | 173–175 | 263.5 | 253 (4.36) | 1665 1700 | 1.28(3H, t, J=7.3, —CH$_2$CH$_3$), 2.55(2H, q, J=2.3, —CH$_2$CH$_3$), 7.71–7.86(2H, m, H-6,7), 8.05–8.23(2H, m, H-5,8) |
| 2d | —CH$_2$CH$_2$CH$_3$ | 90 | 137–138 | 277.5 | 252 (4.22) | 1670 1700 | 1.04(3H, t, J=2.1, —CH$_2$CH$_2$CH$_3$), 1.59–1.99(2H, m, —CH$_2$CH$_2$CH$_3$), 2.50(2H, t, J=7.6, —CH$_2$CH$_2$CH$_3$), 7.69–7.77(2H, m, H-6,7), 8.02–8.20(2H, m, H-5,8) |

TABLE 1-continued

2-Acylamino-3-chloro-1,4-naphthoquinones

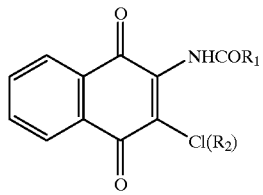

| No. | $R_1$ | Yield (%) | mp °C. | MS ($M^+$) m/z | UV λ max (log ε) | IR $\nu_{C=O}$ | $^1$H-NMR (ppm) |
|---|---|---|---|---|---|---|---|
| 2e | (phenyl) | 80 | 254–256 | 311.5 | 253 (4.50) | 1665 1690 | 7.25–7.45(5H, m, benzene ring), 7.71–7.83(2H, m, H-6,7), 8.08–8.25(2H, m, H-5,8) |
| 2f | (4-F-phenyl) | 65 | 212–214 | 329.5 | 253 (4.67) | 1660 1690 | 7.18(2H, d, J=8.9, H-3',5'), 7.24(2H, d, J=8.9, H-2',6'), 7.75–7.79(2H, m, H-6,7), 8.10–8.13(1H, m, H-5), 8.18–8.21(1H, m, H-6) |
| 2g | (4-OCH$_3$-phenyl) | 61 | 162–164 | 340.5 | 207 (4.40) | 1665 1690 | 3.88(3H, s, —OCH$_3$), 6.98(2H, d, J=8.8, H-3',5'), 7.71–7.81(2H, m, H-6,7), 7.94(2H, d, J=8.8, H-2',6'), 8.05–8.24(2H, m, H-5,8) |
| 2h | (3,5-diOCH$_3$-phenyl) | 63 | 193–194 | 371.5 | 209 (4.53) | 1660 1690 | 3.84(6H, s, —OCH$_3$), 6.67(1H, s, H-4'), 7.06(2H, s, H-2',6'), 7.74–7.79(2H, m, H-6,7), 8.10–8.21(2H, m, H-5,8) |
| 2i | —CH$_2$-(2-F-phenyl) | 66 | 232 | 343 | — | — | 3.88(2H, s, —COCH$_2$), 7.17(2H, t, J=8.5, H-3',5'), 7.29–7.36(1H, m, H-4'), 7.40–7.46(1H, m, H-6'), 7.86–7.92(2H, m, H-6,7), 8.01–8.10(2H, m, H-5,8) |
| 2j | —CH$_2$-(4-F-phenyl) | 54 | 228 | 343 | — | — | 3.80(2H, s, —COCH$_2$), 7.16(2H, t, J=9.0, H-3',5'), 7.36–7.41(2H, m, H-2',6'), 7.85–7.90(2H, m, H-6,7), 7.99–8.08(2H, m, H-5,8) |
| 2k | —(CH$_2$)$_3$COOCH$_3$ | 83 | 127–128 | 335.5 | 254 (4.11) | 1730 | 2.00–2.10(2H, m, —CH$_2$CH$_2$CH$_2$—) 2.45(2H, t, J=7.0, —CH$_2$CH$_2$CH$_2$—) 2.57(2H, t, J=7.0, —CH$_2$CH$_2$CH$_2$—) 3.67(3H, s, —OCH$_3$), 7.71–7.75(2H, m, H-6,7), 8.04–8.07(1H, m, H-5), 8.12–8.15(1H, m, H-8) |
| 2l | —(CH$_2$)$_2$COOCH$_3$ | 81 | 174–175 | 321.5 | 254 (4.33) | 1740 | 2.74–2.82(4H, m, —CH$_2$CH$_2$—), 3.70(3H, s, —OCH$_3$), 7.72–7.76(2H, m, H-6,7), 8.07–8.10(1H, m, H-5), 8.14–8.17(1H, m, H-8) |

TABLE 2

2-Acylamino-3-alkyl (or aryl) amino-1,4-naphthoquinones

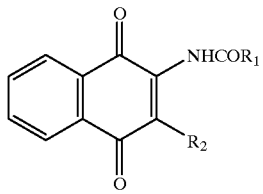

| No. | R$_1$ | R$_2$ | Yield (%) | mp ° C. | MS (M$^+$) m/z | UV λ max (log ε) | IR υ$_{C=O}$ | $^1$H-NMR (ppm) |
|---|---|---|---|---|---|---|---|---|
| 3a | —CH$_3$ | —NH$_2$ | 92 | 233–234 | 230 | 269 (4.22) | 1660 1680 | 2.04(3H, s, —COCH$_3$), 6.78(1H, br, —NH), 7.69–7.84(2H, m, H-6,7), 7.93–7.79(2H, m, H-5,8), 9.58(1H, br, —NHCO—) |
| 3b | —CH$_2$-C$_6$H$_4$-F (ortho) | —NH$_2$ | 75 | 218 | 324 | — | — | 3.79(2H, s, —COCH$_2$—), 6.80(2H, br, s, —NH$_2$), 7.17(2H, tripletoid m, H-3',5'), 7.27–7.34(1H, m, H-4'), 7.46(1H, t, J=7.0, H-6'), 7.73(1H, t, J=7.5, H-6), 7.82(1H, t, J=7.5, H-7), 7.97(1H, d, J=7.5, H-5,8), 9.34(1H, s, —NHCO—) |
| 3c | —CH$_2$-C$_6$H$_4$-F (para) | —NH$_2$ | 83 | 225 | 324 | — | — | 3.71(2H, s, —COCH$_2$—), 6.80(2H, br, s, —NH$_2$), 7.13(2H, t, J=9.0, H-3',5'), 7.41(2H, m, H-2',6'), 7.71(1H, t, J=7.5, H-6), 7.80(1H, t, J=7.5, H-7), 7.94–7.97(2H, m, H-5,8'), 9.35(1H, s, —NHCO—) |
| 29 | —CH$_3$ | —NHCH$_2$CH$_3$ | 88 | 198–200 | 258 | 273 (4.21) | 1650 1670 | 1.27(3H, t, J=7.2, —CH$_2$CH$_3$), 2.24(3H, s, —COCH$_3$), 3.46(2H, q, J=7.2, —CH$_2$—), 7.58–7.72(2H, m, H-6,7), 8.02–8.08(2H, m, H-5,8) |
| 30 | —CH$_3$ | —NHCH(CH$_3$)(CH$_2$CH$_3$) | 83 | 83–84 | 286 | 273 (4.38) | 1660 | 0.93(3H, t, J=7.5, —CH$_2$CH$_3$), 1.21(3H, d, J=6.3, —CHCH$_3$), 1.48–1.64(2H, m, —CH$_2$CH$_3$), 2.24(3H, s, —COCH$_3$), 3.78(1H, m, —NHCH—), 7.58–7.72(2H, m, H-6,7), 8.01–8.06(2H, m, H-5,8) |
| 31 | —CH$_3$ | —NHCH$_2$CH(CH$_3$)$_2$ | 87 | 70–72 | 286 | 273 (4.33) | 1670 | 0.97(6H, d, J=6.9, —(CH$_3$)$_2$), 1.79–1.86(1H, m, —CH—), 2.24(3H, s, —COCH$_3$), 3.26(2H, m, —NHCH$_2$), 7.63–7.71(2H, m, H-6,7), 8.01–8.06(2H, m, H-5,8) |
| 32 | —CH$_3$ | —NHC(CH$_3$)$_3$ | 75 | 76–77 | 286 | 272 (4.24) | 1670 | 1.46(9H, s, —(CH$_3$)$_3$), 2.24(3H, s, COCH$_3$), 7.59–7.72(2H, m, H-6,7), 7.99–8.06(2H, m, H-5,8) |
| 33 | —CH$_3$ | —NHCH(CH$_3$)(CH$_2$CH$_2$CH$_3$) | 83 | 131–132 | 300 | 273 (4.39) | 1670 | 0.92(3H, t, J=7.2, —CH$_2$CH$_3$), 1.21(3H, d, J=6.3, —CHCH$_3$), 1.33–1.60(4H, m, —CHCH$_2$CH$_2$—), 2.24(3H, s, —COCH$_3$), 3.87(2H, mbr, —CH—), 7.57–7.71(2H, m, H-6,7), 8.00–8.06(2H, m, H-5,8) |
| 34 | —CH$_3$ | —NHCH(CH$_2$CH$_3$)$_2$ | 82 | 75–76 | 300 | 272 (4.34) | 1660 | 0.91(3H, t, J=7.6, —CH$_2$CH$_3$), 1.42–1.66(4H, m, —CH$_2$CH$_3$), 2.24(3H, s, —COCH$_3$), 3.72(1H, mbr, —CH—), 7.51–7.77(2H, m, H-6,7), 7.98–8.11(2H, m, H-5,8) |

TABLE 2-continued

2-Acylamino-3-alkyl (or aryl) amino-1,4-naphthoquinones

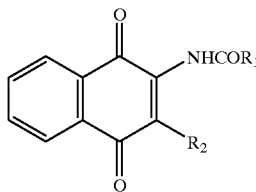

| No. | R$_1$ | R$_2$ | Yield (%) | mp °C. | MS (M$^+$) m/z | UV λ max (log ε) | IR υ$_{C=O}$ | $^1$H-NMR (ppm) |
|---|---|---|---|---|---|---|---|---|
| 35 | —CH$_3$ | —NHCH$_2$CH$_2$CH(CH$_3$)$_2$ | 86 | 128–129 | 300 | 273 (4.24) | 1665 | 0.93(6H, d, J=5.4, —(CH$_3$)$_2$), 1.46–1.74(3H, m, —CH$_2$CH—), 2.25(3H, s, —COCH$_3$), 3.36–3.59(2H, m, —NHCH$_2$), 7.59–7.71(2H, m, H-6,7), 7.96–8.08(2H, H-5,8) |
| 36 | —CH$_3$ | —NHC(CH$_3$)$_2$(CH$_2$CH$_3$) | 73 | 77–79 | 300 | 273 (4.31) | 1670 | 0.93(3H, t, J=7.8, —CH$_2$CH$_3$), 1.39(6H, s, —(CH$_3$)$_2$—), 1.78(2H, q, J=7.8, —CH$_2$CH$_3$), 2.24(3H, s, —COCH$_3$), 7.57–7.71(2H, m, H-6,7), 8.00–8.06(2H, m, H-5,8) |
| 37 | —CH$_3$ | —NHCH$_2$CH(CH$_3$)(CH$_2$CH$_3$) | 86 | 70–71 | 300 | 273 (4.29) | 1660 | 0.83–1.08(6H, m, —CHCH$_3$, —CH$_2$CH$_3$), 1.19–1.77(3H, m, —CH—, —CH$_2$CH$_3$), 2.24(3H, s, —COCH$_3$), 3.23–3.43(1H, br, —NHCH$_2$—), 7.60–7.77(2H, m, H-6,7), 7.96–8.10(2H, m, H-5,8) |
| 38 | —CH$_3$ | —NHCH$_2$C(CH$_3$)$_3$ | 82 | 197–199 | 300 | 272 (4.29) | 1670 | 0.98(9H, s, —(CH$_3$)$_3$), 2.25(3H, s, —COCH$_3$), 3.30(2H, d, J=5.8, —NHCH$_2$—), 7.50–7.77(2H, m, H-6,7), 7.97–8.10(2H, m, H-5,8) |
| 39 | —CH$_3$ | —NHCH$_2$CH$_2$N(CH$_3$)$_2$ | 90 | 195–198 | 301 | 271 (4.26) | 1670 | 2.08(3H, s, —COCH$_3$), 2.77(6H, s, —N(CH$_3$)$_2$), 3.23–3.81(4H, m, —CH$_2$CH$_2$—), 7.72–8.03(2H, m, H-6,7, H-5,8) |
| 40 | —CH$_3$ | —NHCH$_2$CH$_2$OH | 91 | 166–168 | 274 | 271 (4.38) | 1650 | 2.01(3H, s, —COCH$_3$), 3.30(2H, t, J=5.3, —NHCH$_2$—), 3.51(2H, m, —CH$_2$OH), 4.88(1H, br, —OH), 7.72–8.03(2H, m, H-6,7, H-5,8) |
| 41 | —CH$_3$ | —HNH$_2$C—⟨C$_6$H$_4$⟩—OCH$_3$ | 86 | 156–158 | 350 | 273 (4.19) | 1650 1700 | 1.82(1H, br, —NHCH$_2$—), 2.28(3H, s, —COCH$_3$), 3.79(3H, s, —OCH$_3$), 5.56(2H, d, J=5.8, —NHCH$_2$—), 6.33(1H, br, —NHCO—), 6.86(2H, d, J=8.8, H-3',-5'), 7.21(2H, d, J=8.8, H-2',-6'), 7.55–7.78(2H, m, H-6,7) 7.84–8.15(2H, m, H-5,8) |
| 42 | —CH$_3$ | —HNH$_2$C—⟨C$_6$H$_4$⟩—Cl | 82 | 159–161 | 354 | 271 (4.18) | 1650 1705 | 1.71(1H, br, —NHCH$_2$—), 2.29(3H, s, —COCH$_3$), 4.61(2H, d, J=5.8, —NHCH$_2$—), 6.43(1H, br, —NHCO—), 7.15–7.28(4H, m, H-2',3', H-5',6'), 7.60–7.79(2H, m, H-6,7), 7.96–8.22(2H, m, H-5,8) |
| 43 | —CH$_3$ | —NHCH$_2$CH$_2$Cl | 93 | 192–194 | 291.5 | 270 (4.32) | 1665 | 2.23(3H, s, —COCH$_3$), 3.65(2H, t, J=5.8, —CH$_2$Cl), 3.79(2H, m, —NHCH$_2$—), 7.58–7.71(2H, m, H-6,7), 7.99–8.05(2H, m, H-5,8) |

TABLE 2-continued

2-Acylamino-3-alkyl (or aryl) amino-1,4-naphthoquinones

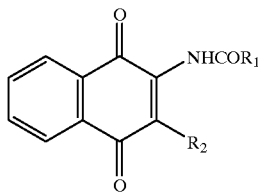

| No. | R₁ | R₂ | Yield (%) | mp °C. | MS (M⁺) m/z | UV λ max (log ε) | IR υ$_{C=O}$ | ¹H-NMR (ppm) |
|---|---|---|---|---|---|---|---|---|
| 44 | —CH₂Cl | —NHCH₂CH₃ | 85 | 185–187 | 292 | 270 (4.80) | 1665 | 1.25(3H, t, J=7.2, —CH₂CH₃), 3.41–3.48(2H, m, —CH₂CH₃), 4.22(2H, s, —COCH₂), 7.59–7.69(2H, m, H-6,7), 7.99–8.07(2H, m, H-5,8) |
| 45 | —CH₂CH₃ | —NHCH₂CH₃ | 93 | 194–196 | 272 | 272 (4.23) | 1660 | 1.24(6H, t, J=7.3, —COCH₂CH₃, —NHCH₂CH₃), 2.48(2H, q, J=7.3, —COCH₂CH₃), 3.33–3.61(2H, m, —NHCH₂CH₃), 7.56–7.70(2H, m, H-6,7), 7.97–8.10(2H, m, H-5,8) |
| 46 | —CH₂CH₂CH₃ | —NHCH₂CH₃ | 91 | 172–174 | 286 | 273 (4.30) | 1670 | 1.02(3H, t, J=7.3, —CH₂CH₂CH₃), 1.25(3H, t, J=7.3, —CH₂CH₃), 1.66–1.97(2H, m, —CH₂CH₂CH₃), 2.94(2H, t, J=7.3, —CH₂CH₂CH₃), 3.33–3.64(2H, m, —NHCH₂CH₃), 7.56–7.71(2H, m, H-6,7), 7.97–8.10(2H, m, H-5,8) |
| 47 | —C₆H₅ (phenyl) | —NHCH₂CH₃ | 87 | 89–91 | 320 | 226 (4.45) | 1655 | 1.20(3H, t, —CH₂CH₃), 3.29–3.60(2H, m, —CH₂CH₃), 7.27–7.55 (5H, m, benzene ring), 7.61–7.79(2H, m, H-6,7), 7.88–8.05(2H, m, H-5,8) |
| 48 | 4-F-C₆H₄ | —NHCH₂CH₃ | 82 | 181–183 | 338 | 271 (4.57) | 1670 | 1.21(3H, t, J=7.2, —CH₂CH₃), 3.40–3.47(2H, m, —CH₂CH₃), 7.08(2H, d, J=8.6, H-3',5'), 7.11(2H, d, J=8.6, H-2',6'), 7.55–7.69(2H, m, H-6,7), 7.90–7.95(1H, m, H-5), 7.98–8.14(1H, m, H-8) |
| 49 | 4-OCH₃-C₆H₄ | —NHCH₂CH₃ | 82 | 159–161 | 350 | 271 (4.23) | 1670 | 1.23(3H, t, J=7.3, —CH₂CH₃), 3.47(2H, m, —CH₂CH₃), 3.86(3H, s, —OCH₃), 6.94(2H, d, J=9.0, H-3',5'), 7.56–7.70(2H, m, H-6,7), 7.91(2H, d, J=9.0, H-2',6'), 7.88–8.10(2H, m, H-5,8) |
| 50 | 3,5-(OCH₃)₂-C₆H₃ | —NHCH₂CH₃ | 84 | 187–189 | 80 | 211 (4.76) | 680 | 1.22(3H, t, J=7.2, —CH₂CH₃), 3.41–3.48(2H, m, —CH₂CH₃), 3.83(6H, s, —OCH₃), 6.61(1H, s, H-4'), 7.04(2H, s, H-2',6'), 7.59–7.68(2H, m, H-6,7), 8.01–8.06(2H, m, H-5,8) |
| 51 | —(CH₂)₃COOCH₃ | —HNCH₂-C₆H₅ | 87 | 151–152 | 406 | 271 (4.45) | 1730 | 1.71–1.75(2H, m, —CH₂CH₂CH₂—), 2.23(2H, t, J=6.9, —CH₂CH₂CH₂—), 2.84(2H, t, J=7.1, —CH₂CH₂CH₂—), 3.58(3H, s, —OCH₃), 4.63(2H, d, J=6.5, —NHCH₂), 7.20–7.30(5H, m, H-2',3',4',5',6'), 7.70–7.80(2H, m, H-6,7), 7.92–7.98(2H, m, H-5,8), 8.85(1H, s, —NHCO—) |

TABLE 2-continued

2-Acylamino-3-alkyl (or aryl) amino-1,4-naphthoquinones

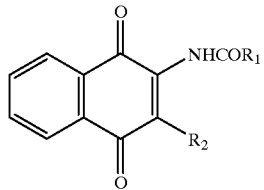

| No. | $R_1$ | $R_2$ | Yield (%) | mp °C. | MS ($M^+$) m/z | UV λ max (log ε) | IR $\nu_{C=O}$ | $^1$H-NMR (ppm) |
|---|---|---|---|---|---|---|---|---|
| 52 | —(CH$_2$)$_3$COOCH$_3$ | —NH—C$_6$H$_5$ | 85 | 182–184 | 392 | 280 (4.42) | 1740 | 2.47–2.53(2H, m, —CH$_2$CH$_2$CH$_2$—), 2.87(2H, t, J=7.2, —CH$_2$CH$_2$CH$_2$—), 3.20(2H, t, J=7.2, —CH$_2$CH$_2$CH$_2$—), 3.64(3H, s, —OCH$_3$), 8.09–8.19(3H, m, H-2',4',6'), 8.32–8.37(2H, m, H-3',5'), 8.91–9.12(2H, m, H-6,7), 9.13–9.18(2H, m, H-5,8), 10.04(1H, s, —NHCO), 10.19(1H, s, —NH—) |
| 53 | —(CH$_2$)$_3$COOCH$_3$ | —NH—C$_6$H$_4$—OCH$_3$ | 86 | 117–118 | 422 | 281 (4.40) | 1730 | 1.35–1.40(2H, m, —CH$_2$CH$_2$CH$_2$—), 1.72(2H, t, J=7.3, —CH$_2$CH$_2$CH$_2$—), 2.07(2H, t, J=7.3, —CH$_2$CH$_2$CH$_2$—), 3.56(3H, s, —COOCH$_3$), 3.72(3H, s, 4'-OCH$_3$), 6.77(2H, d, J=7.4, H-3',5'), 6.91(2H, d, J=7.4, H-2',6'), 7.74–7.85(2H, m, H-6,7), 7.96–8.02(2H, m, H-5,8), 8.81(1H, s, —NHCO—), 8.86(1H, s, —NH—) |
| 54 | —(CH$_2$)$_2$COOCH$_3$ | —NH—C$_6$H$_5$ | 84 | 182–184 | 378 | 280 (4.47) | 1710 | 1.91–2.03(4H, m, —CH$_2$CH$_2$—), 3.51(3H, s, —OCH$_3$), 6.94(2H, d, J=7.6, H-2',6'), 7.00–7.19(1H, m, H-4'), 7.16–7.24(2H, m, H-3',5'), 7.77–7.84(2H, m, H-6,7), 7.98–8.04(2H, m, H-5,8), 8.90(1H, s, —NHCO—), 9.22(1H, s, —NH—) |
| 55 | —(CH$_2$)$_2$COOCH$_3$ | —HNH$_2$C—C$_6$H$_5$ | 89 | 151–152 | 392 | 272 (4.43) | 1730 | 2.48–2.54(4H, m, —CH$_2$CH$_2$—), 3.56(3H, s, —OCH$_3$), 4.59(2H, d, J=5.8, —NHCH$_2$—), 7.22–7.33(5H, m, H-2',3',4',5',6'), 7.72–7.81(2H, m, H-6,7), 7.92–7.94(2H, m, H-5,8), 8.97(1H, s, —NHCO—) |
| 56 | —(CH$_2$)$_2$COOCH$_3$ | —NH—C$_6$H$_4$—OCH$_3$ | 86 | 172–173 | 408 | 281 (4.53) | 1710 | 1.93(2H, t, J=7.2, —CH$_2$CH$_2$—), 2.05(2H, t, J=7.2, —CH$_2$CH$_2$—), 3.52(3H, s, —COCH$_3$), 3.72(3H, s, 4'-OCH$_3$), 6.79(2H, d, J=8.9, H-3',5'), 6.90(2H, d, J=8.9, H-2',6'), 7.75–7.83(2H, m, H-6,7), 7.96–8.03(2H, m, H-5,8), 8.89(1H, s, —NHCO—), 9.03(1H, s, —NH—) |

TABLE 3

1,2-Disubstituted naphth[2,3-d]imidazole-4,9-diones

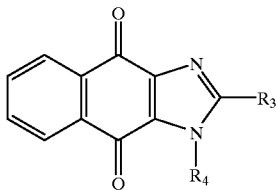

| No. | R₃ | R₄ | Yield % | mp °C. | MS (M⁺) m/z | UV λ max (log ε) | IR $\nu_{C=O}$ | ¹H-NMR (ppm) |
|---|---|---|---|---|---|---|---|---|
| 4a | —CH₃ | —H | 98 | 369–370 | 212 | 247 (4.19) | 1680 1660 | 2.28(3H, s, 2-CH₃), 7.61–7.64(2H, m, H-6,7), 7.89–7.93(2H, m, H-5,8) |
| 4b | —CH₂—(2-F-C₆H₄) | —H | 47 | 278–279 | 306 | — | — | 4.17(2H, s, —CH₂—, 7.14–7.20(2H, m, H-3',5'), 7.29–7.41(2H, m, H-4',6'), 7.76(2H, dd, J=5.0, 3.0, H-6,7), 8.02(2H, dd, J=5.0, 3.0, H-5,8), 14.00(1H, s, —NH) |
| 4c | —CH₂—(4-F-C₆H₄) | —H | 46 | 270–275 | 306 | — | — | 4.13(2H, s, —CH₂—), 7.15(2H, t, J=9.0, H-3',5'), 7.38(2H, dd, J=8.5, 6.0, H-2',6'), 7.83(2H, dd, J=5.5, 3.0, H-6,7), 8.04(2H, m, H-5,8), 13.90(1H, s, =NH) |
| 5 | —CH₃ | —CH₂CH₃— | 66 75 | 185–186 | 240 | 247 (4.64) | 1660 | 1.45(3H, t, J=7.5, —CH₂CH₃, 2.58(3H, s, 2-CH₃), 4.44(2H, q, J=7.5, —CH₂—), 7.69–7.72(2H, m, H-6,7), 8.07–8.09(1H, m, H-5), 8.17–8.20(1H, m, H-8) |
| 6 | —CH₃ | —CH(CH₃)(CH₂CH₃) | 76 | 111–112 | 268 | 248 (4.64) | 1655 1670 | 0.85(3H, t, J=7.0, —CH₂CH₃, 1.65(3H, d, J=7.1, —CHCH₃), 1.86–2.29(3H, m, —CHCH₂—), 2.64(3H, s, 2-CH₃), 4.81(1H, m, N—CH—), 7.65–7.75(2H, m, H-6,7), 8.09–8.25(2H, m, H-5,8) |
| 7 | —CH₃ | —CH₂CH(CH₃)₂ | 77 | 160–161 | 268 | 248 (4.64) | 1650 1670 | 0.99(6H, d, J=6.6, —(CH₃)₂), 2.19(1H, m, —CH—), 2.57(3H, s, 2-CH₃), 4.19(2H, d, J=7.6, —CH₂—), 7.63–7.74(2H, m, H-6,7), 8.02–8.23(2H, m, H-5,8) |
| 8 | —CH₃ | —C(CH₃)₃ | 61 | 120–122 | 268 | 249 (4.58) | 1665 | 1.86(9H, s, —(CH₃)₃), 2.81(3H, s, 2-CH₃), 7.64–7.74(2H, m, H-6,7), 8.02–8.25(2H, m, H-5,8) |
| 9 | —CH₃ | CH(CH₃)(CH₂CH₂CH₃) | 70 | liq. | 282 | 248 (4.56) | 1650 | 0.90(3H, t, J=6.1, —CH₂CH₃, 1.15–1.40(2H, m, —CH₂CH₃), 1.63(3H, d, J=6.9, —CHCH₃), 1.83–2.21(2H, m, —CH₂CH₂—), 2.64(3H, s, 2-CH₃), 4.13(1H, m, N—CH—), 7.65–7.75(2H, m, H-6,7), 8.09–8.25(2H, m, H-5,8) |
| 10 | —CH₃ | —CH(CH₂CH₃)₂ | 70 | 130–131 | 282 | 248 (4.68) | 1665 1670 | 0.83(6H, t, J=7.6, —CH₂CH₃, 1.88–2.10(4H, m, —CH₂), 2.64(3H, s, 2-CH₃), 4.06(1H, m, N—CH—), 7.66–7.76(2H, m, H-6,7), 8.09–8.27(2H, m, H-5,8) |
| 11 | —CH₃ | —CH₂CH₂CH(CH₃)₂ | 73 | 112–113 | 282 | 248 (4.69) | 1655 | 1.03(6H, d, J=5.7, —(CH₃)₃), 1.60–1.73(3H, m, —CH₂CH—), 2.55(3H, s, 2-CH₃), 4.36(2H, t, J=7.5, —N—CH₂—), 7.62–7.72(2H, m, H-6,7), 8.01–8.22(2H, m, H-5,8) |

TABLE 3-continued 1,2-Disubstituted naphth[2,3-d]imidazole-4,9-diones

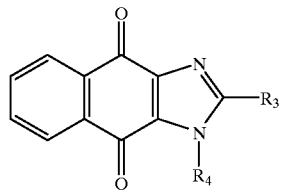

| No. | R₃ | R₄ | Yield % | mp ° C. | MS (M⁺) m/z | UV λ max (log ε) | IR $v_{C=O}$ | ¹H-NMR (ppm) |
|---|---|---|---|---|---|---|---|---|
| 12 | —CH₃ | —C(CH₃)₂(CH₂CH₃) | 58 | liq. | 282 | 248 (4.52) | 1660 | 0.82(3H, t, J=7.6, —CH₂CH₃), 1.83(6H, s, —(CH₃)₂), 2.28(2H, q, J=7.6, —CH₂CH₃), 2.56(3H, s, 2-CH₃), 7.64–7.75(2H, m, H-6,7), 8.09–8.28(2H, m, H-5,8) |
| 13 | —CH₃ | —CH₂CH(CH₃)(CH₂CH₃) | 73 | 146–147 | 282 | 248 (4.65) | 1665 1670 | 0.88–1.04(6H, m, —CH₂CH₃, —CHCH₃), 1.19–1.48(2H, m, —CH₂CH₃), 2.56(3H, s, 2-CH₃), 4.16–4.28(2H, m, N—CH₂—), 7.64–7.79(2H, m, H-6,7), 8.04–8.25(2H, m, H-5,8) |
| 14 | —CH₃ | —CH₂C(CH₃)₃ | 69 | 198–200 | 282 | 248 (4.59) | 1660 | 1.01(9H, s, —(CH₃)₃), 2.59(3H, s, 2-CH₃), 4.35(2H, s, N—CH₂—), 7.64–7.79(2H, m, H-6,7), 8.04–8.25(2H, m, H-5,8) |
| 15 | —CH₃ | —CH₂CH₂N(CH₃)₂ | 78 | 45–46 | 283 | 248 (4.55) | 1650 | 2.32(6H, s, N—(CH₃)₂), 2.59(3H, s, 2-CH₃), 2.69(2H, t, J=6.8, —CH₂CH₃), 4.46(2H, t, J=6.8, —CH₂CH₂—), 7.65–7.75(2H, m, H-6,7), 8.06–8.26(2H, m, H-5,8) |
| 16 | —CH₃ | —CH₂CH₂OH | 77 | 276–277 | 256 | 248 (4.54) | 1655 | 2.54(3H, s, 2-CH₃), 3.73–3.76(2H, m, —CH₂OH), 4.42(2H, t, J=5.4, —NCH₂—), 5.03(1H, br, —OH), 7.83–7.87(2H, m, H-6,7), 8.04–8.10(2H, m, H-5,8) |
| 17 | —CH₃ | —CH₂—C₆H₄—CH₃ | 63ᶜ | 159–161 | 316 | 248 (4.51) | 1660 1680 | 2.31(3H, s, 4'-CH₃), 2.51(3H, s, 2-CH₃), 5.65(2H, s, —CH₂—), 7.04(2H, d, J=9, H-2',6'), 7.14(2H, d, J=9, H-3',5'), 7.69–7.74(2H, m, H-6,7), 8.09–8.13(1H, m, H-5), 8.22–8.25(1H, m, H-8) |
| 18 | —CH₃ | —CH₂—C₆H₄—OCH₃ | 76 | 168–170 | 332 | 247 (4.59) | 1645 1670 | 2.53(3H, s, 2-CH₃), 3.77(3H, s, 2-OCH₃), 5.62(2H, s, —CH₂—), 6.85(2H, d, J=8.7, H-2',6'), 7.12(2H, d, J=8.7, H-3',5'), 7.69–7.73(2H, m, H-6,7), 8.11–8.13(1H, m, H-5), 8.14–8.25(1H, m, H-8) |
| 19 | —CH₃ | —CH₂—C₆H₄—F | 75ᶜ | 168–171 | 320 | 248 (4.65) | 1650 1670 | 2.51(3H, s, 2-CH₃), 5.68(2H, s, —CH₂—), 6.81–7.44(4H, m, H-3',4',5',6'), 7.65–7.75(2H, m, H-6,7), 8.03–8.27(2H, m, H-5,8) |
| 20 | —CH₃ | —CH₂—C₆H₄—Cl | 62ᶜ 73 | 228–229 | 336 | 247 (4.57) | 1645 1670 | 2.48(3H, s, 2-CH₃), 5.62(2H, s, —CH₂—), 7.06(2H, d, J=8.4, H-2',6'), 7.27(2H, d, J=8.4, H-3',5'), 7.68–7.71(2H, m, H-6,7), 8.07–8.10(1H, m, H-5), 8.21–8.23(1H, m, H-8) |

TABLE 3-continued 1,2-Disubstituted naphth[2,3-d]imidazole-4,9-diones

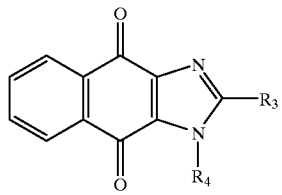

| No. | $R_3$ | $R_4$ | Yield % | mp ° C. | MS ($M^+$) m/z | UV λ max (log ε) | IR $\upsilon_{C=O}$ | $^1$H-NMR (ppm) |
|---|---|---|---|---|---|---|---|---|
| 21 | —$CH_3$ | —$CH_2CH_2Cl$ | 67 | 200–202 | 274 | 248 (4.42) | 1660 1675 | 2.64(3H, s, 2-$CH_3$), 3.95(2H, t, J=5.7, —$CH_2Cl$), 4.66(2H, t, J=5.7, —$NCH_2$—), 7.68–7.72(2H, m, H-6,7), 8.06–8.09(1H, m, H-5), 8.18–8.22(1H, m, H-8) |
| 22 | —$CH_2Cl$ | —$CH_2CH_3$ | 65 | 183–185 | 274 | 247 (4.50) | 1660 1680 | 1.52(3H, t, J=7.2, —$CH_2CH_3$), 4.51(2H, q, J=7.2, —$CH_2CH_3$), 4.75(2H, s, —$CH_2Cl$), 7.66–7.69(2H, m, H-6,7), 8.06–8.09(1H, m, H-5), 8.15–8.18(1H, m, H-8) |
| 23 | —$CH_2CH_3$ | —$CH_2CH_3$ | 78 | 166–167 | 254 | 248 (4.28) | 1660 1675 | 1.46(6H, t, J=7.3, —$COCH_2CH_3$—N—$CH_2CH_3$), 2.86(2H, q, J=7.3, —$CH_2CH_3$), 4.45(2H, q, J=7.3, —$NCH_2CH_3$), 7.64–7.79(2H, m, H-6,7), 8.05–8.26(2H, m, H-5,8) |
| 24 | —$CH_2CH_2CH_3$ | —$CH_2CH_3$ | 79 | 108–109 | 268 | 248 (4.33) | 1665 1680 | 1.06(3H, t, J=7.3, —$CH_2CH_2CH_3$), 1.46(3H, t, J=7.3, —$NCH_2CH_3$), 1.72–2.13(2H, m, —$CH_2CH_2CH_3$), 2.81(2H, t, J=6.8, —$CH_2CH_2CH_3$), 4.44(2H, q, J=7.3, —$NCH_2CH_3$), 7.63–7.78(2H, m, H-6,7), 7.97–8.28(2H, m, H-5,8) |
| 25 | phenyl | —$CH_2CH_3$ | 66 | 153–155 | 302 | 254 (4.47) | 1660 1680 | 1.48(3H, t, J=7.1, —$CH_2CH_3$), 1.49(2H, q, J=7.1, —$CH_2CH_3$), 7.47–7.50(3H, m, H-3',4',5'), 7.66–7.71(5H, m, H-2',6',8', H-6,7), 8.10–8.13(1H, m, H-5), 8.19–8.23(1H, m, H-8) |
| 26 | 4-F-phenyl | —$CH_2CH_3$ | 63 | 06–208 | 320 | 256 (4.73) | 1660 1675 | 1.49(3H, t, J=7.1, —$CH_2CH_3$), 4.50(2H, q, 7.1, —$CH_2CH_3$), 7.19(2H, d, J=8.4, H-3',5'), 7.69–7.73(4H, m, H-2',6', H-6,7), 8.13–8.16(1H, m, H-5), 8.23–8.25(1H, m, H-8) |
| 27 | 4-$OCH_3$-phenyl | —$CH_2CH_3$ | 64 | 190–191 | 332 | 271 (4.50) | 1660 1680 | 1.52(3H, t, J=7.1, —$CH_2CH_3$), 3.87(3H, s, —$OCH_3$), 4.52(2H, q, J=7.1, —$CH_2CH_3$), 7.34(2H, d, J=11.5, H-3',5'), 7.63–7.76(4H, m, H-2',6',8', H-6,7), 8.10–8.29(2H, m, H-5,8) |
| 28 | 3,5-di-$OCH_3$-phenyl | —$CH_2CH_3$ | 67 | 200–202 | 362 | 211 (4.76) | 1660 1680 | 1.49(3H, t, J=7.1, —$CH_2CH_3$), 3.82(6H, s, —$OCH_3$), 4.52(2H, q, J=7.1, —$CH_2CH_3$), 6.58(1H, s, H-4'), 6.80(2H, s, H-2',6'), 7.69–7.72(2H, m, H-6,7), 8.13–8.16(1H, m, H-5), 8.22–8.25(1H, m, H-8) |

TABLE 3-continued 1,2-Disubstituted naphth[2,3-d]imidazole-4,9-diones

| No. | R₃ | R₄ | Yield % | mp °C. | MS (M⁺) m/z | UV λ max (log ε) | IR ν$_{C=O}$ | ¹H-NMR (ppm) |
|---|---|---|---|---|---|---|---|---|
| 57 | —(CH₂)₃COOH | —CH₂—C₆H₅ | 82 | 176–178 | 374 | 249 (4.65) | 1720 | 1.85–1.95(2H, m, —CH₂CH₂CH₂—), 2.52(2H, t, J=7.2, —CH₂CH₂CH₂—), 2.77(2H, t, J=7.2, —CH₂CH₂CH₂—), 5.71(2H, s, —CH₂—), 7.16–7.18(2H, m, H-2',6'), 7.26(3H, m, H-3',4',5'), 7.78–7.81(2H, m, H-6,7), 7.98–8.05(2H, m, H-5,8), 12.02(1H, s, —OH) |
| 58 | —(CH₂)₃COOH | —C₆H₅ | 82 | 228–229 | 360 | 248 (4.58) | 1720 | 1.80–2.05(2H, m, —CH₂CH₂CH₂—), 2.27(2H, t, J=7.5, —CH₂CH₂CH₂—), 2.59(2H, t, J=7.5, —CH₂CH₂CH₂—), 7.53–7.60(5H, m, H-2',3',4',5',6'), 7.78–7.79(2H, m, H-6,7), 7.84–7.88(1H, m, H-5), 8.00–8.13(1H, m, H-8), 11.98(1H, s, —OH) |
| 59 | —(CH₂)₃COOH | —C₆H₄—OCH₃ (4'-) | 83 | 202–204 | 390 | 248 (4.68) | 1720 | 1.86–1.93(2H, m, —CH₂CH₂CH₂—), 2.27(2H, t, J=7.2, —CH₂CH₂CH₂—), 2.57(2H, t, J=7.5, —CH₂CH₂CH₂—), 3.85(3H, s, 4'-OCH3), 7.10(2H, d, J=9, H-3',5'), 7.45(2H, d, J=9, H-2',6'), 7.75–7.85(2H, m, H-6,7), 7.80–8.03(1H, m, H-5), 8.04–8.06(1H, m, H-8), 12.07(1H, s, —OH) |
| 60 | —(CH₂)₂COOH | —C₆H₅ | 83 | 251–252 | 346 | 248 (4.63) | 1730 | 2.70–2.78(4H, m, —CH₂CH₂—), 7.54–7.62(5H, m, H-2',3',4',5',6'), 7.77–7.81(2H, m, H-6,7), 7.87–7.88(1H, m, H-5), 8.05–8.06(1H, m, H-8), 12.21(1H, s-OH) |
| 61 | —(CH₂)₂COOH | —CH₂—C₆H₅ | 85 | 258–259 | 360 | 249 (4.55) | 1730 | 2.75(2H, t, J=7.5, —CH₂CH₂—), 2.93(2H, t, J=7.5, —CH₂CH₂—), 5.75(2H, s, —CH₂—), 7.19–7.34(2H, m, H-2',3',4',5',6'), 7.79–7.81(2H, m, H-6,7), 8.05–8.10(1H, m, H-5), 8.28–8.38(1H, m, H-8), 12.20(1H, s, —OH) |
| 62 | —(CH₂)₂COOH | —C₆H₄—OCH₃ (4'-) | 84 | 187–188 | 376 | 248 (4.55) | 1740 | 2.75(4H, s, —CH₂CH₂—), 3.87(3H, s, 4'-OCH₃) 7.12(2H, d, J=8.7 Hz, H-3',5'), 7.46(2H, d, J=8.7, H-2',6'), 7.76–7.80(2H, m, H-6,7), 7.87–7.90(1H, m, H-5), 8.05–8.07(1H, m, H-8), 12.27(1H, s, —OH) |
| 63 | —CH₂—C₆H₄F (2'-) | —CH₂CH₃ | 72 | 176 | 334 | — | — | 1.29(3H, t, J=7.0 Hz, —CH₂CH₃), 4.31(2H, s, CH₂C₆H₄F), 4.47(2H, q, J=7.0 Hz, —CH₂CH₃), 7.18–7.27(2H, m, H-3',5'), 7.34–7.41(2H, m, H-4',6'), 7.81–7.85(2H, m, H-6,7), 8.02–8.07(2H, m, H-5,8) |

TABLE 3-continued

1,2-Disubstituted naphth[2,3-d]imidazole-4,9-diones

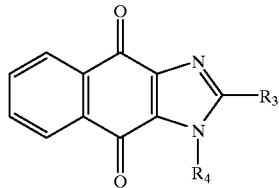

| No. | R$_3$ | R$_4$ | Yield % | mp °C. | MS (M$^+$) m/z | UV λ max (log ε) | IR $\upsilon_{C=O}$ | $^1$H-NMR (ppm) |
|---|---|---|---|---|---|---|---|---|
| 64 | —CH(CH$_2$CH$_3$)—C$_6$H$_4$F (o-F) | —CH$_2$CH$_3$ | 35 | 171 | 362 | — | — | 0.91[3H, t, J=7.5 Hz, —CH(CH$_2$CH$_3$)], 1.06(3H, t, J=7.0 Hz, —OCH$_2$CH$_3$), 2.09 and 2.29[each 1H, m, —CH(CH$_2$CH$_3$)], 4.35(2H, m, —OCH$_2$CH$_3$), 4.54[1H, t, J=7.5 Hz, —CH(CH$_2$CH$_3$)], 7.19–7.34(4H, m, H-3'-6'), 7.81–7.84(2H, m, H-6,7), 8.02–8.09(2H, m, H-5,8) |
| 65 | —CH(CH$_2$CH$_3$)—C$_6$H$_4$F (p-F) | —CH$_2$CH$_3$ | 29 | 160 | 362 | — | — | 0.88[3H, t, J=7.0 Hz, —CH(CH$_2$CH$_3$)], 1.06(3H, t, J=7.0 Hz, —OCH$_2$CH$_3$), 2.02 and 2.28[each 1H, m, —CH(CH$_2$CH$_3$)], 4.34[1H, t, J=7.5 Hz, —CH(CH$_2$CH$_3$)], 4.39(2H, m, —OCH$_2$CH$_3$), 7.17(2H, m, J=9.0 Hz, H-3',5'), 7.41–7.45(2H, m, H-2',6'), 7.79–7.85(2H, m, H-6,7), 8.00–8.10(2H, m, H-5,8) |
| 66 | —CH$_2$—C$_6$H$_4$F (p-F) | —CH$_2$CH$_3$ | 76 | 178 | 334 | — | — | 1.17(3H, t, J=7.0 Hz, —CH$_2$CH$_3$), 4.30(2H, s, CH$_2$C$_6$H$_4$F), 4.40(2H, q, J=7.0 Hz, —CH$_2$CH$_3$), 7.14–7.20(2H, m, H-3',5'), 7.35–7.40(2H, m, H-2',6'), 7.77–7.83(2H, m, H-6,7), 7.98–8.07(2H, m, H-5,8) |

TABLE 4

1,2-Disubstituted naphth[2,3-d]imidazole-4,9-diones

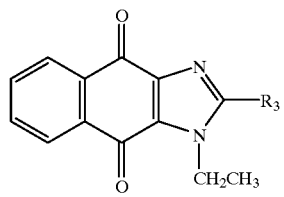

| No. | R$_3$ | Yield % | mp °C. | MS (M$^+$) m/z | UV λ max (log ε) | IR $\upsilon_{C=O}$ | $^1$H-NMR (ppm) |
|---|---|---|---|---|---|---|---|
| 63 | —CH$_2$—C$_6$H$_4$F (o-F) | 72 | 176 | | | | 1.29(3H, t, J=7.0 Hz, —CH$_2$CH$_3$), 4.31(2H, s, CH$_2$C$_6$H$_4$F), 4.47(2H, q, J=7.0 Hz, —CH$_2$CH$_3$), 7.18–7.27(2H, m, H-3',5'), 7.34–7.41(2H, m, H-4',6'), 7.81–7.85(2H, m, H-6,7), 8.02–8.07(2H, m, H-5,8) |

TABLE 4-continued 1,2-Disubstituted naphth[2,3-d]imidazole-4,9-diones

| No. | R₃ | Yield % | mp °C. | MS (M⁺) m/z | UV λ max (log ε) | IR $v_{C=O}$ | ¹H-NMR (ppm) |
|---|---|---|---|---|---|---|---|
| 64 | CHCH₂CH₃–(2-F-phenyl) | 35 | ? | | | | 0.91[3H, t, J=7.5 Hz, —CH(CH₂CH₃)], 1.06(3H, t, J=7.0 Hz, —OCH₂CH₃), 2.09 and 2.29[each 1H, m, —CH(CH₂CH₃)], 4.35(2H, m, —OCH₂CH₃), 4.54[1H, t, J=7.5 Hz, —CH(CH₂CH₃)], 7.19–7.34(4H, m, H-3'-6'), 7.81–7.84(2H, m, H-6,7), 8.02–8.09(2H, m, H-5,8) |
| 65 | CHCH₂CH₃–(4-F-phenyl) | 29 | ? | | | | 0.88[3H, t, J=7.0 Hz, —CH(CH₂CH₃)], 1.06(3H, t, J=7.0 Hz, —OCH₂CH₃), 2.02 and 2.28[each 1H, m, —CH(CH₂CH₃)], 4.34[1H, t, J=7.5 Hz, —CH(CH₂CH₃)], 4.39(2H, m, —OCH₂CH₃), 7.17(2H, m, J=9.0 Hz, H-3',5'), 7.41–7.45(2H, m, H-2',6'), 7.79–7.85(2H, m, H-6,7), 8.00–8.10(2H, m, H-5,8) |
| 66 | CH₂–(4-F-phenyl) | 76 | 178 | | | | 1.17(3H, t, J=7.0 Hz, —CH₂CH₃), 4.30(2H, s, CH₂C₆H₄F), 4.40(2H, q, J=7.0 Hz, —CH₂CH₃), 7.14–7.20(2H, m, H-3',5'), 7.35–7.40(2H, m, H-2',6'), 7.77–7.83(2H, m, H-6,7), 7.98–8.07(2H, m, H-5,8) |

TABLE 5

Inhibition of In Vitro Ovarian Cancer Cell Growth by 2 ·66
cytotoxicity log $GI_{50}(M)^{a,b}$

| Compd. | IGROV1 | OVCAR-3 | OVCAR-4 | OVCAR-5 | OVCAR-8 | SK-OV-3 |
|---|---|---|---|---|---|---|
| 2e | −4.66 | −4.72 | | | | NT |
| 2f | −5.77 | | | | | NT |
| 2g | | −5.79 | | | | |
| 2h | −5.86 | | | | | |
| 2i | −6.17 | | −6.22 | NT | | NT |
| 2j | −5.73 | | | NT | −5.71 | NT |
| 4b | NT | −4.84 | −4.55 | NT | | NT |
| 4c | −4.90 | −5.27 | −4.83 | NT | | NT |
| 5 | | −7.30 | −6.49 | −6.11 | −6.31 | |
| 6 | | −4.49 | | NT | | |
| 7 | | −4.60 | | NT | | |
| 8 | | −4.41 | | NT | | |
| 10 | | −4.49 | | NT | | |
| 14 | | −4.18 | | NT | | |
| 15 | | −5.15 | | NT | | |
| 16 | −4.69 | −4.61 | −4.58 | NT | | |
| 17 | | | | NT | −5.52 | |
| 19 | | −4.82 | | NT | | |
| 20 | | | | NT | −5.05 | |
| 21 | −4.94 | | −4.83 | | | −5.28 |
| 22 | | | | | | −6.29 |
| 23 | −4.61 | −4.73 | | | | NT |
| 24 | −4.57 | −4.49 | −4.49 | | | −4.66 |
| 25 | | −5.23 | −4.90 | | −4.85 | |
| 26 | | −4.47 | | | | −4.68 |
| 28 | | | | | | −5.41 |

TABLE 5-continued

Inhibition of In Vitro Ovarian Cancer Cell Growth by 2 · 66 cytotoxicity log $GI_{50}(M)^{a,b}$

| Compd. | IGROV1 | OVCAR-3 | OVCAR-4 | OVCAR-5 | OVCAR-8 | SK-OV-3 |
|---|---|---|---|---|---|---|
| 3b |  | −5.08 |  | NT |  | NT |
| 3c | −4.71 | −4.88 |  | NT | −4.47 | NT |
| 30 |  | −4.39 |  |  |  |  |
| 31 |  | −4.78 |  |  |  |  |
| 32 |  | −4.81 |  |  |  |  |
| 37 |  | −4.25 |  | NT |  |  |
| 38 |  | −4.26 |  | NT |  |  |
| 39 |  |  | −5.05 | NT | −4.95 |  |
| 40 |  | −4.72 |  | NT |  |  |
| 41 |  | −5.09 | −5.09 | NT |  |  |
| 43 |  |  |  |  | −4.70 |  |
| 44 | NT | −4.75 | −4.77 |  |  | NT |
| 45 |  | −4.49 |  |  |  |  |
| 46 |  | −4.47 |  | NT |  |  |
| 47 |  | −4.47 |  |  |  | −4.62 |
| 48 | −4.50 | −4.44 |  |  | −4.49 | −4.73 |
| 49 |  | −4.62 | −4.46 |  | −4.61 |  |
| 50 |  | −6.28 |  |  |  | −6.77 |
| 51 |  | −4.64 |  |  |  |  |
| 52 |  | −4.90 |  |  |  |  |
| 53 | −4.74 | −5.20 | −4.75 | −4.73 |  |  |
| 54 |  | −5.52 |  | −5.41 |  |  |
| 55 | −4.75 | −5.40 | −4.73 |  |  |  |
| 56 |  | −5.48 |  |  |  |  |
| 57 |  | −4.67 | −4.69 |  |  |  |
| 58 |  | −4.47 | −4.62 |  |  |  |
| 59 |  | −4.48 |  |  |  |  |
| 60 |  |  |  |  |  |  |
| 61 |  | −4.55 |  |  |  |  |

[a]Data obtained from NCI's in vitro disease-oriented tumor cells screen
[b]NT = not tested

TABLE 6

Inhibition of In Vitro Non-Small Cell Lung Cancer Cell Growth by 2 · 66 cytotoxicity log $GI_{50}(M)$

| Compd. | EKVX | HOP-18 | HOP-62 | HOP-92 | NCI-H266 | NCI-H23 | NCI-H460 | NCI-H522 | LXFL 529 |
|---|---|---|---|---|---|---|---|---|---|
| 2e |  |  | NT | −4.60 | −4.61 | −4.62 |  | −4.62 | NT |
| 2f |  |  | NT | −5.79 | −5.96 |  |  | −6.34 | NT |
| 2g |  |  | NT | −5.82 | −5.87 |  |  | −6.42 | NT |
| 2h |  |  | NT |  |  |  |  | −6.49 | NT |
| 2i |  | −6.18 |  |  |  | −6.25 | −6.15 | −6.67 | −6.40 |
| 2j |  |  | NT | −5.72 |  | −5.89 |  | NT |  |
| 4b |  |  |  |  |  | −4.56 | −4.47 | −4.67 | −4.50 |
| 5 |  |  |  | −5.79 |  | −5.81 |  | −6.62 |  |
| 6 |  | NT |  | −4.66 |  | −4.48 | −4.71 |  | −4.48 |
| 7 |  | NT |  | −4.99 |  | −4.74 | −4.63 | −4.58 |  |
| 8 |  | NT |  | −5.03 |  | −4.42 | −4.44 | −4.36 |  |
| 9 |  | NT |  | −4.78 |  | −4.81 | −5.34 |  | −4.90 |
| 10 |  | NT |  | −4.65 |  | −4.67 | −4.68 |  | −4.71 |
| 11 |  | NT |  |  |  |  | −5.22 |  | −4.88 |
| 12 |  | NT |  | NT |  |  | −4.91 |  | −4.86 |
| 13 |  | NT |  | −4.69 |  | −4.68 | −4.83 |  | −4.77 |
| 14 |  | NT |  | −4.78 |  |  | −4.23 |  |  |
| 15 |  | NT |  | NT |  | −4.92 | −5.01 | −5.27 |  |
| 16 |  | NT |  | NT |  | −4.82 |  | −4.84 |  |
| 17 |  | NT |  | NT |  |  | −6.41 | −5.50 | −5.76 |
| 18 |  | NT |  | NT |  |  | −5.62 | −5.22 | −5.37 |
| 19 |  | NT |  | NT |  | −4.88 | −5.39 | −4.97 | −4.87 |
| 20 |  | NT |  | NT |  |  | −5.76 | −5.26 | −5.26 |
| 21 |  | NT |  |  |  |  | −4.83 |  | NT |
| 22 |  | NT |  |  | −6.65 |  |  | −6.53 | NT |
| 23 |  | NT |  |  | −4.54 |  |  |  | NT |
| 24 | NT | NT |  | NT |  |  |  | −4.62 | NT |
| 25 | NT | NT |  |  |  |  |  | −4.82 | NT |
| 27 |  | NT | −4.22 |  |  | −4.21 |  |  | NT |
| 28 |  | NT |  |  |  |  |  | −5.19 | NT |
| 3b |  |  | −4.59 | −4.65 |  |  |  | −4.67 |  |
| 3c |  | NT | −4.56 | −4.48 |  | −4.87 |  | −4.79 |  |

TABLE 6-continued

Inhibition of In Vitro Non-Small Cell Lung Cancer Cell Growth by 2·66 cytotoxicity log GI$_{50}$(M)

| Compd. | EKVX | HOP-18 | HOP-62 | HOP-92 | NCI-H266 | NCI-H23 | NCI-H460 | NCI-H522 | LXFL 529 |
|---|---|---|---|---|---|---|---|---|---|
| 31 | | −4.89 | | −4.85 | −4.80 | −4.70 | | NT | −4.79 |
| 32 | | −4.83 | | | −4.84 | | | NT | −4.82 |
| 33 | | NT | | −4.32 | | | | −4.19 | |
| 34 | | NT | | −6.47 | | | | | |
| 36 | | NT | | NT | | −4.72 | | −4.99 | |
| 37 | | NT | | NT | | −4.17 | | | |
| 38 | | NT | | NT | | | | −4.72 | |
| 39 | | NT | | NT | | −4.94 | −4.89 | −4.99 | |
| 40 | | NT | | NT | | | | −4.61 | |
| 41 | | NT | | −5.81 | | −5.17 | | −5.86 | |
| 42 | | NT | | NT | | | | −6.01 | |
| 43 | | NT | | | | −4.58 | | −4.69 | NT |
| 44 | −4.80 | NT | −4.78 | | | | | −4.82 | NT |
| 45 | | NT | | | | | | −4.34 | NT |
| 46 | | NT | | | | | | −4.59 | NT |
| 47 | | NT | | | | | | −4.95 | NT |
| 48 | | NT | | | | −4.46 | | −4.68 | NT |
| 49 | | NT | | | | −4.36 | | −4.51 | NT |
| 50 | | NT | | −5.95 | | | −6.20 | −6.43 | NT |
| 52 | | NT | NT | | NT | −4.97 | | | NT |
| 53 | | NT | NT | | NT | −4.69 | −4.80 | | NT |
| 55 | | NT | NT | −4.80 | | −4.67 | −4.74 | −4.72 | NT |
| 56 | | NT | | −5.66 | | | −5.18 | | NT |
| 57 | −4.50 | NT | NT | | NT | −4.50 | | −4.53 | NT |
| 58 | | NT | NT | | NT | | | −4.85 | NT |
| 59 | | NT | NT | −4.69 | NT | −4.36 | | −4.59 | NT |
| 60 | | NT | | −7.65 | | | | −4.42 | NT |
| 61 | | NT | | −5.26 | | −4.52 | −4.42 | −4.61 | NT |
| 62 | | NT | | NT | | | | −4.46 | NT |
| 65 | | | | −4.75 | −4.82 | | | | |
| 66 | | | | −4.97 | | | −4.90 | −5.06 | |

TABLE 7

Inhibition of In Vitro CNS Cancer Cell Growth by 2·66 cytotoxicity log GI$_{50}$(M)

| Compd. | SF-268 | SF-295 | SF-539 | SNB-19 | SNB-75 | SNB-78 | U 251 | XF-498 |
|---|---|---|---|---|---|---|---|---|
| 2f | | | | | | NT | −5.73 | NT |
| 2g | | | | | | NT | −5.83 | NT |
| 2i | −6.34 | | −6.62 | | −6.33 | NT | −6.48 | |
| 2j | | | −5.65 | | −5.66 | NT | | −5.71 |
| 4b | | | −4.51 | −4.42 | | NT | | −5.10 |
| 5 | −6.48 | | | | | | −5.72 | |
| 6 | −4.51 | | −4.49 | | | | | |
| 7 | | | −4.61 | | | | | |
| 8 | | | | | −4.50 | | | −4.36 |
| 9 | | | −4.89 | | | | −4.91 | |
| 10 | | | | | −4.69 | | | −4.60 |
| 11 | −4.84 | | −4.92 | | | | −4.90 | |
| 12 | | | | | | | | −4.77 |
| 13 | | | −4.75 | | | | | |
| 17 | −5.46 | | −5.88 | | | | −5.73 | |
| 18 | −5.35 | | −5.42 | | | | −5.20 | |
| 19 | −5.34 | | −5.16 | | | | −5.18 | |
| 20 | −5.29 | | −5.60 | | | −5.03 | −5.46 | |
| 21 | | | | | −4.84 | NT | −4.90 | NT |
| 23 | | | | | −4.68 | NT | | NT |
| 25 | NT | | | | −4.61 | NT | | NT |
| 28 | | −4.53 | | | −4.65 | NT | | |
| 3b | −4.46 | −4.49 | −4.57 | −4.45 | −4.73 | NT | −4.44 | −4.59 |
| 3c | −4.54 | | | −4.63 | −4.49 | NT | −5.09 | |
| 31 | −4.69 | | −4.76 | | −4.77 | | | −4.85 |
| 32 | | | −4.80 | | −4.86 | | | −4.95 |
| 36 | | | −4.61 | | | | | −4.84 |
| 38 | | | −4.48 | | | | | −4.59 |
| 39 | | | −4.93 | | | | −4.99 | |
| 41 | | | −5.13 | | | | | −5.47 |
| 42 | | | −5.36 | | | | | −5.84 |
| 43 | | | | | −4.61 | NT | | NT |

TABLE 7-continued

Inhibition of In Vitro CNS Cancer Cell Growth by 2·66
cytotoxicity log GI$_{50}$(M)

| Compd. | SF-268 | SF-295 | SF-539 | SNB-19 | SNB-75 | SNB-78 | U 251 | XF-498 |
|---|---|---|---|---|---|---|---|---|
| 50 |  | −6.85 | −5.99 |  |  | NT | −6.28 | NT |
| 51 |  | NT | −4.44 |  |  | NT |  | NT |
| 53 |  |  | −4.71 |  |  | NT |  | NT |
| 54 |  |  | −5.11 |  |  | NT |  | NT |
| 55 |  |  | −4.70 | −4.66 |  | NT |  | NT |
| 57 | −4.58 | −4.59 |  |  | NT | NT |  | NT |
| 58 | −4.42 |  |  |  | −4.36 | NT |  | NT |
| 61 |  |  | −4.55 |  |  | NT |  | NT |
| 64 |  |  |  |  | −4.60 |  | −5.07 |  |
| 65 |  |  |  |  |  |  | −4.71 | −4.70 |
| 66 |  |  | −4.88 |  | −4.80 |  |  |  |

TABLE 8

Inhibition of In Vitro Melanoma Cell Growth by 2·66
cytotoxicity log GI$_{50}$(M)

| Compd. | LOXIMVI | MALME-3M | M14 | M19-MEL | SK-MEL-2 | SK-MEL-28 | SK-MEL-5 | UACC-257 | UACC-62 |
|---|---|---|---|---|---|---|---|---|---|
| 2e | NT | −4.77 |  | NT | NT |  |  | NT | −4.62 |
| 2f | NT | −5.82 |  | NT | NT |  | NT | −5.71 | −6.55 |
| 2g | NT | −5.92 | −6.20 | NT | NT | −6.17 | −5.89 | −5.79 | −6.12 |
| 2h | NT |  | −6.26 | NT | NT | −5.85 | −5.89 |  | −6.82 |
| 2i | NT |  | −6.29 | −6.36 | −6.21 | −6.34 | NT | −6.41 | −6.48 |
| 2j | NT | −5.67 |  |  |  |  | NT |  |  |
| 4b | NT |  |  | −4.71 |  |  | NT |  |  |
| 4c | NT | −4.84 | −4.82 |  | −4.86 |  | NT |  |  |
| 6 | −4.64 | −4.49 |  | −4.74 |  |  | −4.57 | −4.55 | −4.55 |
| 7 |  | −4.69 |  | −4.80 | −4.59 |  | −4.73 | −4.75 | −4.68 |
| 8 | −4.38 | −4.35 |  | −4.61 |  |  | −4.41 | −4.37 | −4.35 |
| 9 | −5.06 |  |  | −4.90 |  |  | −4.88 |  | −5.17 |
| 10 | −4.71 | −4.58 |  | −4.83 | −4.56 |  | −4.80 | −4.62 | −4.99 |
| 11 | −4.83 |  |  | −4.84 |  |  | −4.84 |  | −4.91 |
| 12 | −4.71 |  |  | −4.80 | −4.73 |  | −4.80 |  | −4.87 |
| 13 | −4.71 |  |  | −4.47 |  |  | −4.82 |  | −5.00 |
| 14 | −4.25 |  |  | −4.47 |  |  | −4.37 |  |  |
| 15 |  | −5.55 | −4.93 | −5.69 | −4.91 |  | −5.13 |  | −4.92 |
| 16 | −4.63 | −4.93 | −4.67 | −5.59 | −4.74 |  | −4.95 | −4.78 | −4.78 |
| 17 | −6.22 |  |  |  |  |  |  |  | −5.95 |
| 18 | −5.60 |  |  |  |  |  |  |  | −5.34 |
| 19 | −5.14 | −5.05 |  | −5.44 |  |  | −4.99 |  | −5.28 |
| 20 | −5.69 |  |  | −4.93 |  |  |  |  | −5.47 |
| 21 | NT | −5.24 | −5.33 | NT | NT |  | NT | −4.85 | −4.89 |
| 22 | NT | −5.98 |  | NT | NT |  | −6.38 |  | −5.89 |
| 23 | NT | −4.81 | −4.63 | NT | NT |  | NT | −4.60 | −4.54 |
| 24 | NT | −4.65 |  | NT | NT |  | −4.53 | −4.74 | −4.59 |
| 25 | NT | −5.06 | −4.81 | NT | NT |  | −4.95 | −5.41 |  |
| 26 | NT | −4.35 | −4.15 | NT | NT |  |  |  |  |
| 28 | NT |  |  | NT | NT |  |  |  | −4.69 |
| 3b | NT | −4.87 |  | −5.35 | −4.84 |  | NT | −4.53 | −4.42 |
| 3c | NT |  |  | −5.16 |  |  | NT |  |  |
| 30 | −4.81 |  |  |  |  |  |  |  |  |
| 31 | −4.81 | −4.72 | −4.74 | −4.73 |  | −4.77 | −4.70 | −4.73 | −4.74 |
| 32 | −4.78 |  | −4.77 | −4.81 |  |  | −4.80 |  | −4.86 |
| 33 |  | −4.44 |  | −4.20 |  |  | −4.13 |  |  |
| 36 | −4.53 | −4.54 |  | −4.88 | −4.68 |  | −4.87 | −4.69 | −4.60 |
| 37 |  | −4.45 |  | −4.68 |  |  | −4.50 |  |  |
| 38 |  | −4.46 |  | −4.68 |  |  | −4.40 | −4.30 | −4.41 |
| 39 | −4.90 | −5.12 |  | −5.12 |  |  | −5.14 | −5.03 | −4.98 |
| 40 |  | −4.89 |  | −5.01 |  |  | −4.53 |  |  |
| 41 | −5.07 | −5.08 |  | −5.02 | −5.04 |  | −5.13 | −5.06 | −5.11 |
| 42 |  |  |  | −5.28 | −5.25 | −5.26 | −5.26 | −5.21 | −5.58 |
| 43 | NT | −4.86 | −4.89 | NT | NT |  | −4.77 | −4.82 | −4.70 |
| 44 | NT |  |  | NT | NT | −4.75 | −4.78 | NT | NT |
| 45 | NT | −4.64 | −4.50 | NT | NT |  | −4.27 | −4.52 |  |
| 46 | NT | −4.41 | NT | NT | NT |  |  | −4.40 |  |
| 47 | NT | −4.77 | −4.58 | NT | NT |  | NT | −4.63 | −4.70 |
| 48 | NT | −4.72 | −4.61 | NT | NT |  | −4.46 | −4.80 | −4.82 |
| 49 | NT | −4.67 | −4.67 | NT | NT |  | −4.46 | −4.71 | −4.40 |
| 50 | NT | −6.11 |  | NT | NT |  | −6.35 |  | −6.45 |

TABLE 8-continued

Inhibition of In Vitro Melanoma Cell Growth by 2 ·66
cytotoxicity log GI$_{50}$(M)

| Compd. | LOXIMVI | MALME-3M | M14 | M19-MEL | SK-MEL-2 | SK-MEL-28 | SK-MEL-5 | UACC-257 | UACC-62 |
|---|---|---|---|---|---|---|---|---|---|
| 51 |  | −4.81 | −4.53 | NT |  |  | NT | −4.53 | −4.53 |
| 52 |  | −5.45 |  | NT |  |  | NT |  | −5.49 |
| 53 |  | −5.47 | −4.71 | NT | −4.75 | −4.68 | NT | −4.74 | −4.89 |
| 54 |  | −5.76 | −5.71 | NT | −5.41 | −5.59 | NT | −5.56 | −5.75 |
| 55 | −4.66 | NT | −4.73 | NT | −4.73 |  | −4.92 | −4.78 | −4.76 |
| 56 | −5.41 | NT | −5.22 | NT | −5.31 |  | −5.75 | −5.37 | −5.67 |
| 57 |  | −4.80 | −5.43 | NT | −4.83 |  | NT | −4.60 | −4.76 |
| 58 |  | −4.67 | −4.72 | NT |  |  | NT | −4.48 | −4.48 |
| 59 |  | −4.82 | −4.81 | NT |  |  | NT | −4.56 | −4.63 |
| 61 | −4.57 | NT | −4.67 | NT | −4.59 |  | −4.67 | −4.47 | −4.42 |
| 62 | −4.55 | NT |  | NT |  |  |  |  |  |
| 65 |  |  |  |  | −4.77 |  |  |  | −4.95 |
| 66 |  | −4.94 |  | −5.02 |  |  |  | −5.10 |  |

TABLE 9

Inhibition of In Vitro Colon Cancer Cell Growth by 2 ·66
cytotoxicity log GI$_{50}$(M)

| Compd. | COLO-205 | DLD-1 | HCC-2998 | HCT-116 | HCT-15 | HT 29 | KM 12 | KM 20L2 | SW 620 |
|---|---|---|---|---|---|---|---|---|---|
| 2e | −4.81 | NT |  | −4.76 | −4.60 |  |  | NT | −4.76 |
| 2f |  | NT |  | −6.34 | −6.27 |  |  | NT | −6.11 |
| 2g | −5.76 | NT |  | −6.36 | −6.37 |  | −5.82 | NT | −6.17 |
| 2h |  | NT |  | −6.35 | −6.38 |  | −5.92 | NT | −6.24 |
| 2i |  | −6.41 |  | −6.37 |  |  | −6.29 |  |  |
| 2j |  | −5.62 |  |  | −5.64 |  |  |  | −5.68 |
| 4b | −4.47 | −4.79 |  |  |  | −4.49 |  | −4.47 | −4.42 |
| 4c |  | −5.40 |  |  | −5.19 |  |  |  | −4.84 |
| 5 | −6.45 |  |  | −5.91 |  |  | −5.76 |  | −6.17 |
| 6 |  | −4.57 |  | −4.50 | −4.57 |  |  |  |  |
| 7 |  |  |  | −4.68 |  |  |  |  |  |
| 8 |  |  |  |  |  | −4.36 |  |  |  |
| 9 |  | −5.07 |  | −5.26 | −5.22 | −4.76 |  |  |  |
| 10 | −4.57 | −4.61 |  | −4.71 | −5.04 |  |  |  |  |
| 11 | −4.84 | −4.95 |  | −5.17 | −4.93 |  |  |  |  |
| 12 | −4.77 | −4.81 |  | −4.87 | −4.64 |  |  |  |  |
| 13 | −4.70 |  |  |  | −4.76 |  |  |  |  |
| 15 | −5.35 |  |  | −4.89 | −4.98 |  |  | −5.20 |  |
| 16 | −4.72 |  |  | −4.72 |  |  |  |  |  |
| 17 |  | −5.91 |  | −6.12 | −6.21 | −5.90 |  |  | −5.48 |
| 18 |  | −5.33 |  | −5.43 | −5.76 | −5.31 | −5.27 |  |  |
| 19 |  | −5.13 |  | −5.16 | −5.37 | −5.03 |  |  |  |
| 20 |  | −5.38 |  | −5.59 | −5.97 | −5.39 |  | −5.09 | NT |
| 21 | −4.85 | NT |  |  | −5.10 | −4.80 |  | NT |  |
| 23 | −4.77 | NT |  | NT |  | −4.60 |  | NT | −4.57 |
| 24 |  | NT | −4.51 |  | −4.55 | −4.73 |  | NT |  |
| 25 | −4.85 | NT |  |  | −5.05 |  |  | NT |  |
| 3b |  | −4.78 |  |  | −4.62 |  |  |  |  |
| 3c |  | −4.95 |  |  |  |  |  |  |  |
| 30 |  | −4.56 |  |  | −4.34 |  |  |  | −4.65 |
| 31 |  | −4.72 |  | −4.69 | −4.75 |  |  | −4.67 | −4.68 |
| 32 |  | −4.80 |  |  | −4.76 |  |  |  | −4.85 |
| 36 |  |  |  | −4.75 |  |  |  |  |  |
| 38 | −4.41 |  |  | −4.47 | −4.26 |  |  |  |  |
| 39 | −5.00 |  |  | −5.08 | −5.02 |  |  |  |  |
| 40 |  |  |  | −4.52 |  |  |  | −4.62 |  |
| 41 | −5.03 | −5.07 |  | −5.29 |  |  |  |  | −5.09 |
| 42 | −5.27 |  |  | −5.51 | −5.25 |  |  |  |  |
| 43 | −4.55 | NT |  | −4.69 |  | −4.58 |  | NT | −4.60 |
| 44 | NT | NT |  | −4.74 |  | NT | −4.77 | NT |  |
| 45 | −4.33 | NT |  | −4.44 | −4.19 | −4.46 |  | NT | −4.22 |
| 46 | −4.44 | NT |  | −4.36 | −4.40 | −4.36 | −4.28 | NT | −4.48 |
| 47 | −4.78 | NT |  | −4.59 | −4.73 |  |  | NT | −4.63 |
| 48 | −4.58 | NT | −4.46 | −4.52 | −4.51 | −4.65 |  | NT | −4.49 |
| 49 | −4.43 | NT | −4.43 | −4.44 |  | −4.63 |  | NT | −4.36 |
| 50 |  | NT |  | −6.38 | −6.22 | −6.19 | −6.30 | NT | −6.42 |
| 51 | −4.62 | NT | −4.49 |  |  | NT |  | NT |  |
| 52 |  | NT |  |  |  | NT | −5.28 | NT |  |
| 53 |  | NT | −4.69 | −4.71 |  | NT |  | NT |  |

TABLE 9-continued

Inhibition of In Vitro Colon Cancer Cell Growth by 2·66 cytotoxicity log $GI_{50}$(M)

| Compd. | COLO-205 | DLD-1 | HCC-2998 | HCT-116 | HCT-15 | HT 29 | KM 12 | KM 20L2 | SW 620 |
|---|---|---|---|---|---|---|---|---|---|
| 55 | −4.69 | NT | | −4.77 | | NT | | NT | −4.70 |
| 57 | | NT | | −4.54 | | NT | | NT | |
| 58 | | NT | | −4.31 | | NT | −4.50 | NT | |
| 59 | −4.43 | NT | | −4.44 | −4.35 | NT | | NT | |
| 60 | | NT | | −4.30 | | | | NT | |
| 61 | −4.47 | NT | | −4.44 | | | | NT | −4.50 |
| 65 | | −5.69 | | | | | | | |

TABLE 10

Inhibition of In Vitro Leukemia Cell Growth by 2·66 cytotoxicity log $GI_{50}$(M)

| Compd. | CCRF-CEM | HL-60 (TB) | K-562 | MOLT-4 | RPMI-8226 | SR |
|---|---|---|---|---|---|---|
| 2e | | | −4.66 | −4.70 | | |
| 2f | −6.10 | −6.47 | −6.04 | −5.65 | | |
| 2g | −6.10 | −6.35 | −5.85 | | −6.02 | |
| 2h | −6.70 | −7.04 | −6.39 | | −6.31 | −6.33 |
| 2i | −6.54 | −6.55 | −6.53 | −6.60 | −6.44 | −6.32 |
| 2j | NT | −7.56 | NT | NT | −7.07 | −6.88 |
| 4b | | −4.45 | | | | |
| 6 | −4.33 | −4.84 | −4.47 | −4.55 | NT | |
| 7 | | −4.64 | −4.52 | | NT | |
| 8 | | −4.34 | −4.30 | 4.31 | NT | −4.35 |
| 9 | | | −5.07 | | NT | |
| 10 | | −4.97 | −4.68 | | NT | −4.59 |
| 11 | −4.87 | −5.22 | −5.09 | −5.08 | NT | −5.33 |
| 12 | | −5.12 | −4.87 | −4.73 | NT | −5.03 |
| 13 | | −5.30 | −5.27 | −5.54 | NT | −5.55 |
| 14 | | −4.44 | −4.25 | | NT | |
| 15 | | −5.28 | | | NT | −4.93 |
| 16 | | −4.70 | −4.59 | | NT | −4.58 |
| 17 | −5.70 | −5.72 | −6.08 | −6.19 | NT | −6.48 |
| 18 | −5.39 | −5.38 | −5.49 | −5.59 | NT | −5.84 |
| 19 | −4.98 | −5.26 | −5.25 | −5.27 | NT | −5.37 |
| 20 | −5.33 | −5.36 | −5.69 | −5.50 | NT | −5.88 |
| 21 | | −4.79 | −4.80 | −4.89 | | |
| 22 | −6.67 | | | −6.45 | | −6.40 |
| 24 | −4.61 | | −4.51 | −4.77 | −4.50 | |
| 25 | | | | −4.83 | | |
| 3c | −4.55 | −4.59 | | | | |
| 30 | −4.66 | −4.76 | −4.36 | | −4.87 | NT |
| 31 | −5.14 | −5.56 | −4.81 | | | NT |
| 32 | −5.63 | −5.65 | −5.14 | −5.19 | −4.93 | NT |
| 36 | −4.77 | −4.78 | −4.68 | −4.86 | NT | −4.50 |
| 38 | −4.52 | −4.49 | −4.42 | | NT | |
| 39 | | −5.01 | −4.91 | | NT | |
| 40 | | −4.68 | | | NT | |
| 41 | −5.06 | −5.77 | −5.11 | −5.43 | NT | |
| 42 | | −5.86 | −5.61 | −5.62 | NT | |
| 43 | −4.72 | NT | −4.55 | −4.60 | | |
| 45 | −4.25 | | | | | |
| 46 | | −4.39 | −4.29 | | | |
| 48 | −4.45 | | | −4.52 | | |
| 49 | | | | −4.44 | | |
| 50 | −6.17 | −6.39 | −6.31 | −6.12 | | −6.23 |
| 51 | −4.44 | −4.54 | | −4.47 | | |
| 54 | | −5.46 | NT | | | |
| 55 | | −4.66 | | | | |
| 56 | | | | | | −5.16 |
| 57 | −5.28 | −4.54 | | | −4.73 | |
| 58 | −4.39 | −4.43 | | −4.39 | | |
| 59 | −4.44 | −4.51 | | −4.44 | | |
| 64 | | | | −4.62 | | |
| 65 | | −4.74 | −4.73 | −4.68 | | −4.73 |
| 66 | −5.08 | −5.33 | | −4.94 | | |

TABLE 11

Inhibition of In Vitro Prostate Cancer Cell Growth by 2 - 66 cytotoxicity log $GI_{50}$ (M)

| Compd. | PC-3 | DU-145 |
|---|---|---|
| 2e | −4.60 | |
| 2f | −5.95 | |
| 2g | −5.90 | |
| 2h | −6.24 | |
| 2i | | |
| 21 | −5.07 | |
| 23 | −4.73 | |
| 25 | −4.99 | |
| 43 | −4.65 | |
| 44 | −4.80 | NT |
| 45 | −4.37 | |
| 46 | −4.39 | |
| 47 | −4.74 | |
| 48 | −4.76 | |
| 49 | −4.48 | |
| 50 | −6.42 | |
| 53 | NT | −4.79 |

TABLE 12

Inhibition of In Vitro Small Cell Lung Cancer Cell Growth by 2 - 66 cytotoxicity log $GI_{50}$ (M)

| Compd. | DMS 114 | DMS 273 |
|---|---|---|
| 2i | −6.76 | |
| 4b | −4.47 | −4.46 |
| 5 | −6.56 | −5.78 |
| 6 | NT | −4.47 |
| 7 | NT | −4.57 |
| 8 | NT | −4.28 |
| 9 | NT | −5.14 |
| 10 | NT | −4.64 |
| 11 | NT | −4.96 |
| 12 | NT | −4.93 |
| 13 | NT | −5.01 |
| 16 | NT | −4.70 |
| 17 | NT | −5.97 |
| 18 | NT | −5.48 |
| 19 | NT | −5.19 |
| 20 | NT | −5.58 |
| 3c | | −4.47 |
| 30 | −4.55 | −4.56 |
| 31 | −4.83 | −4.84 |
| 39 | NT | −4.93 |
| 66 | | −5.01 |

TABLE 13

Inhibition of In Vitro Breast Cancer Cell Growth by 2·66 cytotoxicity log GI$_{50}$(M)

| Compd. | MCF-7 | MCF7/ADR-RES | MDA-MB-231/ATCC | HS 578T | MDA-MB-435 | MDA-N | BT-549 | T-47D |
|---|---|---|---|---|---|---|---|---|
| 2e | −4.72 | −4.73 | | | −4.72 | −5.30 | −4.70 | −4.66 |
| 2f | | | | | | | | −5.72 |
| 2g | | −5.85 | | | | | −5.77 | −5.90 |
| 2h | | −5.83 | | | | | −5.81 | −5.85 |
| 5 | −6.17 | | | | | | | |
| 21 | | −4.79 | −4.81 | | −4.82 | | | |
| 23 | | | −4.77 | | −4.74 | NT | −4.76 | −4.74 |
| 24 | | −4.58 | | | −4.76 | −4.70 | | −4.55 |
| 25 | | −4.88 | NT | | −4.80 | | | −5.65 |
| 28 | | | | −4.44 | | | | |
| 43 | | | | | −4.78 | −4.67 | | −4.60 |
| 44 | | | | | −4.81 | NT | | |
| 45 | | −4.23 | | | NT | | | |
| 46 | | NT | | | −4.60 | −4.68 | | |
| 47 | | −4.78 | −5.21 | | −5.14 | −5.31 | | −4.85 |
| 48 | −4.52 | −4.56 | | | −4.74 | −4.47 | | |
| 49 | | −4.54 | | | −4.77 | −4.43 | | |
| 50 | −6.43 | −6.34 | | | −6.84 | −6.92 | | |
| 51 | −4.52 | −4.56 | | | −4.37 | −4.38 | −4.54 | |
| 52 | | | | | −5.26 | −5.41 | NT | |
| 53 | −4.77 | | | | −4.74 | −4.68 | −4.71 | |
| 54 | −5.75 | | | | −5.67 | −5.69 | | |
| 55 | −4.76 | | | | −4.72 | −4.79 | | |
| 56 | | | −4.63 | | −5.69 | −5.74 | | |
| 57 | −4.53 | | | | NT | −4.65 | NT | |
| 58 | −4.49 | | | | NT | −4.36 | NT | |
| 59 | −4.49 | | | | −4.58 | −4.50 | −5.06 | |
| 60 | | | | | | | | −4.19 |
| 61 | | | −4.47 | | −4.72 | −4.67 | | |
| 62 | | | | | | | | −4.48 |

TABLE 14

Inhibition of In Vitro Renal Cancer Cell Growth by 2·66 cytotoxicity log GI$_{50}$(M)

| Compd. | 786-0 | ACHN | CAK1-1 | RXF-393 | RXF-631 | SN12C | TK-10 | UO-31 |
|---|---|---|---|---|---|---|---|---|
| 2e | | −4.68 | NT | −4.72 | NT | | −4.64 | NT |
| 2f | | −6.03 | NT | −5.90 | NT | | | NT |
| 2g | | −6.44 | NT | −6.23 | NT | | | NT |
| 2h | | −6.39 | NT | −6.28 | NT | | | NT |
| 2i | | −6.32 | | −6.78 | | | | −6.22 |
| 2j | | −5.70 | | −5.75 | | | | |
| 4b | | | | −4.69 | −4.42 | | −4.53 | |
| 4c | | −4.85 | | −5.16 | | | | |
| 6 | | | NT | −4.57 | NT | | | |
| 7 | | | NT | | NT | | | −4.58 |
| 8 | | −4.31 | NT | | NT | −4.30 | | −4.43 |
| 10 | | | NT | | NT | | | −4.71 |
| 12 | | | NT | −4.68 | NT | | | |
| 16 | | −4.60 | NT | | NT | | | |
| 17 | −5.66 | | NT | | NT | | | |
| 18 | −5.27 | | NT | −4.83 | NT | | | |
| 19 | −4.88 | | NT | | NT | | | |
| 20 | −5.25 | | NT | | NT | | | |
| 23 | | | NT | −4.70 | NT | −4.56 | −4.66 | NT |
| 25 | | | NT | −4.81 | NT | | | NT |
| 26 | | | NT | −4.27 | NT | | | NT |
| 28 | −4.34 | | NT | −4.86 | NT | | | NT |
| 3b | −4.57 | | | −4.46 | −4.44 | | | |
| 3c | | | | −4.68 | | | −4.57 | |
| 31 | −4.84 | | −4.78 | −4.90 | NT | −4.77 | −4.68 | −4.74 |
| 32 | −5.47 | | −4.79 | | NT | | | |
| 35 | | −7.52 | NT | | NT | | | |
| 36 | | −4.82 | NT | −4.60 | NT | | | −4.56 |
| 38 | | −4.57 | NT | −4.43 | | | | −4.33 |

TABLE 14-continued

Inhibition of In Vitro Renal Cancer Cell Growth by 2 ·66 cytotoxicity log GI$_{50}$(M)

| Compd. | 786-0 | ACHN | CAK1-1 | RXF-393 | RXF-631 | SN12C | TK-10 | UO-31 |
|---|---|---|---|---|---|---|---|---|
| 39 | | | NT | | | −4.98 | | |
| 41 | | −5.68 | NT | | −5.19 | | | −5.02 |
| 42 | | −5.74 | NT | −5.37 | | | | −5.29 |
| 44 | | | NT | −4.78 | NT | −4.75 | −4.75 | NT |
| 45 | | | NT | −4.32 | NT | | | NT |
| 46 | | | NT | −4.32 | NT | | | NT |
| 47 | | NT | NT | −4.62 | NT | | | NT |
| 48 | | | NT | −4.53 | NT | | | NT |
| 49 | | | NT | −4.55 | NT | | | NT |
| 50 | −6.23 | −6.01 | NT | −6.49 | NT | | | NT |
| 61 | | | | −4.60 | NT | | −4.47 | −4.51 |
| 64 | | | | −5.53 | | | −5.49 | |
| 65 | | | | −4.83 | −4.71 | −4.90 | | |
| 66 | | −4.85 | | | −4.82 | | | −5.33 |

What is claimed is:

1. A method of inhibiting tumor cell growth sensitive to the naphthoquinone below in a mammalian subject, comprising:
administering to the subject a pharmaceutically effective amount of a naphthoquinone compound represented by formula (I)

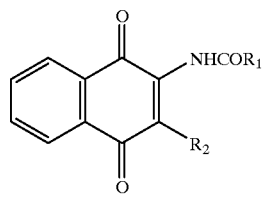

I wherein $R_1$ is lower alkyl, halogenated lower alkyl, phenyl, benzyl, phenethyl, or —(CH$_2$)$_m$COOX, where m is 2 and 3 and H is H, methyl, or ethyl; and $R_2$ is halo or NHY, where Y is hydrogen, lower alkyl, halogenated lower alkyl, hydroxylated lower alkyl, lower dialkylaminoalkyl, phenyl, benzyl, or phenethyl.

2. The method of claim 1, wherein $R_1$ is phenyl or benzyl, and $R_2$ is Cl.

3. The method of claim 2, wherein $R_1$ is 4-fluorophenyl, 4-methoxyphenyl, 3,5-dimethoxyphenyl, 2-fluorophenylmethyl, or 4-fluorophenylmethyl.

4. The method of claim 3, wherein $R_1$ is 3,5-dimethoxyphenyl.

5. The method of claim 3, wherein $R_1$ is 2-fluorophenylmethyl.

6. The method of claim 3, wherein $R_1$ is 4-fluorophenylmethyl.

7. The method of claim 1, wherein $R_1$ is lower alkyl or halogenated lower alkyl, and $R_2$ is NHY, where Y is lower alkyl or halogenated lower alkyl.

8. The method of claim 7, wherein $R_1$ is methyl and $R_2$ is NHY, where Y is —CH (CH$_2$CH$_3$)$_2$.

9. The method of claim 7, wherein $R_1$ is methyl and $R_2$ is NHY, where Y is —CH$_2$CH$_2$N(CH$_3$)$_2$.

10. The method of claim 1, wherein $R_1$ is phenyl and $R_2$ is NHY, where Y is methyl or ethyl, halogenated methyl or ethyl, hydroxyethyl, or —(CH$_2$)$_2$NZ$_2$, where Z is methyl or ethyl.

11. The method of claim 10, wherein $R_1$ is 3,5-dimethoxyphenyl, and $R_2$ is NHY, where Y is ethyl.

12. The method of claim 1, wherein $R_1$ is lower alkyl, halogenated lower alkyl, or —(CH$_2$)$_m$COOX, and $R_2$ is NHY, where Y is phenyl or benzyl.

13. The method of claim 12, wherein $R_1$ is methyl, and Y is (4-methoxyphenyl)methyl or (4-chlorophenol)methyl.

14. The method of claim 12, wherein $R_1$ is —(CH$_2$)$_m$COOX.

15. The method of claim 14, wherein X is methyl or ethyl and m is 2, and $R_2$ is NHY, where Y is unsubstituted phenyl or 4-methoxyphenyl.

* * * * *